United States Patent
Ibrahim et al.

(10) Patent No.: US 9,814,714 B2
(45) Date of Patent: Nov. 14, 2017

(54) KINASE MODULATION, AND INDICATIONS THEREFOR

(71) Applicant: Plexxikon Inc., Berkeley, CA (US)

(72) Inventors: Prabha N. Ibrahim, Mountain View, CA (US); Chao Zhang, Moraga, CA (US); Wayne Spevak, Berkeley, CA (US); Jiazhong Zhang, Foster City, CA (US); Guoxian Wu, Palo Alto, CA (US); Jack Lin, Hercules, CA (US); Hanna Cho, Oakland, CA (US); Marika Nespi, Berkeley, CA (US); Songyuan Shi, Fremont, CA (US); Todd Ewing, Walnut Creek, CA (US); Ying Zhang, Fremont, CA (US); Gideon Bollag, Orinda, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 15/160,729

(22) Filed: May 20, 2016

(65) Prior Publication Data

US 2016/0339025 A1 Nov. 24, 2016

Related U.S. Application Data

(60) Provisional application No. 62/165,813, filed on May 22, 2015.

(51) Int. Cl.
*C07D 239/42* (2006.01)
*A61K 31/506* (2006.01)
*A61K 45/06* (2006.01)
*A61K 31/519* (2006.01)

(52) U.S. Cl.
CPC .......... *A61K 31/506* (2013.01); *A61K 31/519* (2013.01); *A61K 45/06* (2013.01)

(58) Field of Classification Search
CPC .................................................. C07D 401/12
USPC ........................................................ 514/256
See application file for complete search history.

(56) References Cited

U.S. PATENT DOCUMENTS

| | | |
|---|---|---|
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 2014/0128373 A1 | 5/2014 | Ibrahim et al. |
| 2014/0357612 A1 | 12/2014 | Zhang et al. |
| 2016/0068528 A1 | 3/2016 | Zhang et al. |
| 2016/0075712 A1 | 3/2016 | Shi et al. |
| 2016/0176865 A1 | 6/2016 | Ibrahim et al. |
| 2016/0326162 A1 | 11/2016 | Lin et al. |
| 2016/0326168 A1 | 11/2016 | Ibrahim et al. |
| 2016/0340357 A1 | 11/2016 | Ibrahim et al. |
| 2016/0340358 A1 | 11/2016 | Ibrahim |
| 2017/0029413 A1 | 2/2017 | Holladay et al. |
| 2017/0056382 A1 | 3/2017 | Wu et al. |
| 2017/0081326 A1 | 3/2017 | Ibrahim et al. |

OTHER PUBLICATIONS

International Search Report and Written Opinion for International Application No. PCT/US2016/033587 dated Jul. 26, 2016, 16 pages.
Le et al., "Selective RAF inhibitor impairs ERK1/2 phosphorylation and growth in mutant NRAS, vemurafenib-resistant melanoma cells", Pigment Cell Melanoma Res. 2013; 26(4): 509-517.
Basile et al., "Inhibition of mutant BRAF splice variant signaling by next generation, selective RAF inhibitors", Pigment Cell Melanoma Res. 2014; 27(3): 479-484.
Choi et al., "Identification of PLX4032-resistance mechanisms and implications for novel RAF inhibitors", Pigment Cell & Melanoma Research, vol. 27, Issue 2, pp. 253-262.
Zhang et al., "RAF inhibitors that evade paradoxical MAPK pathway activation", Macmillan Publishers Limited, 2015, vol. 526, Nature.

*Primary Examiner* — Raymond Henley, III
(74) *Attorney, Agent, or Firm* — Sheppard Mullin Richter & Hampton LLP

(57) ABSTRACT

The present disclosure provides methods of treating a subject suffering from or at risk of a BRAF V600 mutation or BRAF fusion mutation related disease or condition, without activating the MAPK pathway or inducing expression of MAPK pathway genes in cells harboring wild-type BRAF.

31 Claims, 5 Drawing Sheets

KINASE MODULATION, AND INDICATIONS THEREFOR

CROSS-REFERENCE TO RELATED APPLICATIONS

This application claims the benefit under 35 U.S.C. §119 (e) of U.S. Provisional Application 62/165,813, filed on May 22, 2015, which is hereby incorporated by reference in its entirety.

FIELD

This disclosure relates generally to methods of treating a subject suffering from or at risk of a BRAF V600 mutation or BRAF fusion mutation related disease or condition, without activating the MAPK pathway or inducing expression of MAPK pathway genes in cells harboring wild-type BRAF.

BACKGROUND

Efforts have been made to develop agents that block mutated B-Raf kinase (BRAF) to provide substantial therapeutic improvement in personalized treatment of melanoma. Examples of specific BRAF inhibitors that are currently in medical use include vemurafenib and dabrafenib. Dabrafenib has been shown to have objective tumor response. Moreover, it has been demonstrated and well documented that vemurafenib has an overall survival benefit in mutant $BRAF^{V600}$ melanoma. For the clinical effectiveness of cancer therapy using BRAF inhibitors, it desirable to achieve complete abolition of MAPK pathway output in tumors having BRAF V600E mutations. However, these first generation BRAF inhibitors paradoxically activate the MAPK pathway having oncogenic RAS or increased receptor signaling. The V600E missense mutation in (BRAF) leads to an anomalous regulation of the MAPK pathway, uncontrolled cell proliferation, and initiation of tumorigenesis. While the ATP-competitive B-Raf inhibitors block the MAPK pathway in B-Raf mutant cells, they induce conformational changes to wild-type B-Raf kinase domain leading to heterodimerization with C-Raf, causing a paradoxical as hyperactivation of MAPK pathway. While vemurafenib favors the mutant V600E form of BRAF, binding to wild-type BRAF can induce BRAF/CRAF heterodimers resulting in ERK1/2 activation. The negative consequences of this "paradoxical activation" of ERK1/2 includes cellular proliferation leading to progression of keratoacanthomas (KAs) and cutaneous squamous cell carcinomas (cuSCC), and this progression has been observed to occur within weeks of initiation of therapy with these BRAF inhibitors. Accordingly, there is a need for a new generation of $BRAF^{V600}$ mutant inhibitors that avoids paradoxical activation of MAPK signaling, thereby inhibiting the ERK1/2 pathway to achieve fewer and less serious side effects and to improve safety and duration of patient response.

SUMMARY

Disclosed is a new use of a class of BRAF inhibitors, which have been found to inhibit mutant RAF cells without activating the MAPK pathway, at exceptional and unexpected levels, in cells containing an upstream activation event. The BRAF inhibitors of the present disclosure can inhibit both BRAF point mutations and fusion mutations. Accordingly, the present disclosure overcomes the obstacles that are present in the first generation BRAF inhibitors that are currently in use.

Specifically, the present disclosure relates to a method of treating a subject suffering from or at risk of a BRAF V600 mutation or a BRAF fusion mutation related disease or condition without activating the MAPK pathway or inducing expression of MAPK pathway genes in cells harboring wild-type BRAF, comprising administering to the subject a therapeutically effective amount of a compound of Formula I or II:

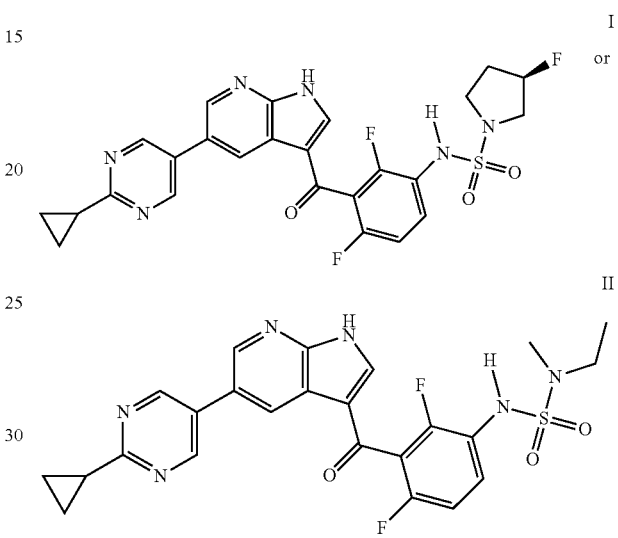

or a pharmaceutically acceptable salt, isomer, tautomer or deuterated form thereof.

Another embodiment of the disclosure relates to a method of treating a subject suffering from or at risk of a BRAF V600 mutation or a BRAF fusion mutation related disease or condition without activating the MAPK pathway or inducing expression of MAPK pathway genes in cells harboring wild-type BRAF, comprising administering to the subject a pharmaceutical composition comprising a therapeutically effective amount of a compound of Formula I or Formula II, or a pharmaceutically acceptable salt, isomer, tautomer or deuterated form thereof, and a pharmaceutically acceptable excipient or carrier.

Another embodiment of the disclosure relates to a method of treating a subject suffering from or at risk of a BRAF V600 mutation or a BRAF fusion mutation related disease or condition without activating the MAPK pathway or inducing expression of MAPK pathway genes in cells harboring wild-type BRAF, comprising administering to the subject a pharmaceutical composition comprising a therapeutically effective amount of a compound of Formula I or Formula II, or a pharmaceutically acceptable salt, isomer, tautomer or deuterated form thereof, and another therapeutic agent.

Additional embodiments will be apparent from the following Drawings and Detailed Description and from the claims.

DETAILED DESCRIPTION

I. Definitions

Figure 1A:
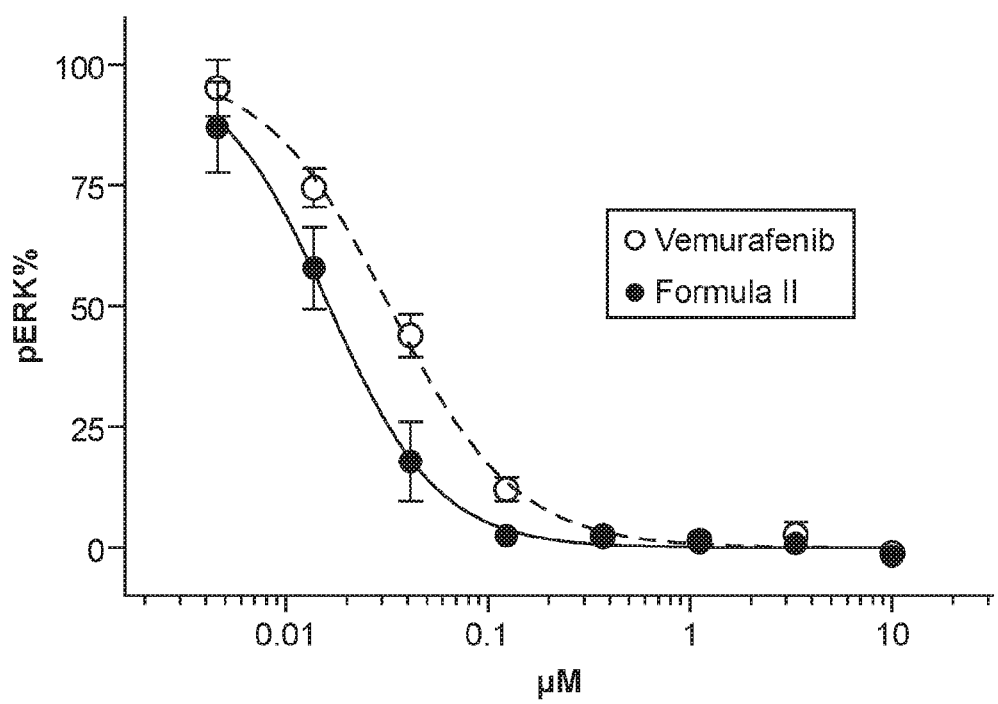
FIG. 1(A) shows that Formula II (filled in circle; bottom line) and vemurafenib (open circle; dashed top line) have similar potency to block pERK signaling in human BRAF$^{V600E}$ melanoma cell COLO829.

As used herein the following definitions apply unless clearly indicated otherwise:

As used herein, the terms "treat," "treating," "therapy," "therapies," and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

In the present context, the term "therapeutically effective" or "effective amount" indicates that a compound or amount of the compound of Formula I or Formula II when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

As used herein, the terms "non-stimulation," "non-activation," and "non-inducement" as applied to the compound of Formula I or II with respect to the MAPK (i.e., the MAPK pathway or expression of MAPK pathway genes in cells harboring wild-type BRAF) refers to less stimulation, less activation, and less inducement, as compared to the stimulation, activation and inducement that is observed with first generation BRAF V600E inhibitors such as dabrafenib and vemurafenib.

As used herein, the term "solid form" refers to a solid preparation (i.e. a preparation that is neither gas nor liquid) of a pharmaceutically active compound that is suitable for administration to an intended animal subject for therapeutic purposes. The compound of Formula I or Formula II disclosed herein is intended to included solid forms of Formula I and Formula II, respectively. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. The compounds of Formula I and Formula II disclosed herein are intended to include semi-crystalline forms of compounds of Formula I and Formula II. In one embodiment of the present disclosure, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailability. Such a mixture may provide both rapid and extended exposure to the active compound.

As used herein, the term "complex" refers to a combination of the compound of Formula I or Formula II, and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

As used herein, the term "biopharmaceutical properties" refers to the pharmacokinetic action of a compound or complex of the present disclosure, including the dissolution, absorption and distribution of the compound on administration to a subject. As such, certain solid forms of compounds of the disclosure, such as amorphous complexes of compounds of the disclosure, are intended to provide improved dissolution and absorption of the active compound, which is typically reflected in improved $C_{max}$ (i.e. the maximum achieved concentration in the plasma after administration of the drug) and improved AUC (i.e. area under the curve of drug plasma concentration vs. time after administration of the drug).

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.).

The compound of Formula I and Formula II can each exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. The compound of Formula I and Formula II for use in accordance with the present disclosure may each exist in multiple crystalline or amorphous forms. In general, all physical forms are equivalent for the uses contemplated by the present disclosure and are intended to be within the scope of the present disclosure.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. The therapeutically effective amount will vary depending on the compound, the disorder or condition and its severity and the age, weight, etc., of the mammal to be treated. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

As used herein, the term "modulating" or "modulate" refers to an effect of altering a biological activity, especially a biological activity associated with a particular biomolecule such as a protein kinase. For example, an inhibitor of a particular biomolecule modulates the activity of that biomolecule, e.g., an enzyme, by decreasing the activity of the biomolecule, such as an enzyme. Such activity is typically indicated in terms of an inhibitory concentration ($IC_{50}$) of the compound for an inhibitor with respect to, for example, an enzyme.

As used herein, the term "protein kinase mediated disease or condition," refers to a disease or condition in which the biological function of a protein kinase, including any mutations thereof, affects the development, course, and/or symptoms of the disease or condition, and/or in which modulation of the protein kinase alters the development, course, and/or symptoms of the disease or condition. The protein kinase mediated disease or condition includes a disease or condition for which inhibition provides a therapeutic benefit, e.g. wherein treatment with protein kinase inhibitor(s), including one or more of a compound of Formula I or Formula II as described herein, provides a therapeutic benefit to the subject suffering from or at risk of the disease or condition.

As used herein, the term "BRAF V600 mutation related disease or condition" or "BRAF V600 mutation mediated disease or condition" refers to a disease or condition in which the biological function of a BRAF kinase having a V600 mutation affects the development, course, and/or symptoms of the disease or condition, and/or in which modulation of the BRAF alters the development, course, and/or symptoms of the disease or condition. The BRAF V600 mutation related disease or condition or BRAF V600 mutation mediated disease or condition includes a disease or condition for which inhibition provides a therapeutic benefit, e.g. wherein treatment with a protein kinase inhibitor(s), including one or more of a compound of Formula I or Formula II as described herein, provides a therapeutic benefit to the subject suffering from or at risk of the disease or condition.

As used herein, the term "BRAF fusion mutation related disease or condition" or "BRAF fusion mutation mediated disease or condition" refers to a disease or condition in which the biological function of a BRAF kinase having a fusion mutation affects the development, course, and/or symptoms of the disease or condition, and/or in which modulation of the BRAF alters the development, course, and/or symptoms of the disease or condition. The BRAF fusion mutation related disease or condition or BRAF fusion mutation mediated disease or condition includes a disease or condition for which inhibition provides a therapeutic benefit, e.g. wherein treatment with a protein kinase inhibitor(s), including one or more of a compound of Formula I or Formula II as described herein, provides a therapeutic benefit to the subject suffering from or at risk of the disease or condition.

In addition, abbreviations used herein have respective meanings as follows:

| | |
|---|---|
| BRAF | v-Raf murine sarcoma viral oncogene homolog B1 |
| Cmax | maximum observed concentration |
| $EC_{50}$ | half maximal effective concentration |
| ERK | extracellular signal-regulated kinases |
| $IC_{50}$ | half maximal inhibitory concentration |
| KRAS2 | v-Ki-ras2 Kirsten rat sarcoma viral oncogene homolog |

II. Paradox Activation of First Generation BRAF Inhibitors

The identification of activating BRAF V600E mutations (primarily missense substitutions for Valine-600 or BRAFV600) in cancer (Davies 2002) supports a functionally important role for BRAF in the pathogenesis of these malignancies. Specific BRAF inhibitors including vemurafenib (Bollag 2010; Flaherty 2010) and dabrafenib (Stellwagen 2011) have demonstrated both objective tumor response (Sosman 2012; Hauschild 2012) and, in the case of vemurafenib, overall survival benefit in mutant BRAFV600 driven melanoma (Chapman 2011). The clinical effectiveness of BRAF inhibitor-based therapy depends on complete abolition of the MAPK pathway output in tumors harboring BRAF V600E mutations (Bollag 2010). However, the first generation BRAF inhibitors paradoxically activate the MAPK pathway in cells bearing oncogenic RAS or elevated upstream receptor signaling (Hatzivassiliou 2010; Heidorn 2010; Poulikakos 2010). This activation can lead to cellular proliferation and has been associated clinically with appearance of cutaneous squamous cell carcinomas (cuSCC) and keratoacanthomas (KAs), sometimes within weeks of initiation of therapy (Su 2012; Anforth 2012; Hauschild 2012; Huang 2012). These MAPK pathway activation-induced tumors have uncharacteristically high incidence of RAS mutations (Oberholzer 2012; Su 2012). Although BRAF inhibitors in clinical testing have shown a relative lack of toxicity, the paradoxical activation mechanism might accelerate progression of other RAS driven cancers, and recent case reports of increased incidence of primary melanomas (Zimmer 2012) and progression of RAS-mutant leukemia (Callahan 2012) during BRAF inhibitor treatment demonstrates this.

Activating mutations in BRAF fuel cancer growth by constitutively promoting MAPK pathway signaling independent of RAS activation. Efforts to develop agents to block mutated BRAF have brought dramatic therapeutic improvement in personalized treatment of metastatic melanoma. However, the development of these agents also revealed an unexpected consequence of these targeted therapies: stimulated growth of certain cancers (paradoxical activation). So far the most common side effect examples are skin neoplasms originating from keratinocytes (Robert 2011), first observed with sorafenib (Lacouture 2006) and more recently with vemurafenib (Flaherty 2010; Huang 2012) and dabrafenib (Hauschild 2012). In the context of fatal metastatic diseases, the appearance of nonmalignant skin tumors such as keratoacanthoma and keratoacanthoma-like cuSCCs may be acceptable, especially since most lesions are easy to identify and remove. However, the appearance of these secondary malignancies highlights the two opposing effects of RAF inhibitors: they both cure and cause tumors. Structurally-diverse ATP-competitive RAF kinase inhibitors can both inhibit and paradoxically activate the RAF/MEK/ERK pathway depending on whether the pathway is activated by a BRAF V600E mutation or by an upstream event, such as RAS mutation or receptor tyrosine kinase activation (Hatzivassiliou 2010; Heidorn 2010; Poulikakos 2010).

There is also a link between EGFR signaling and BRAF inhibitor-induced skin carcinogenesis. Inducing expression of MAPK pathway response genes induces EGFR ligands. Vemurafenib significantly induces the expression of EGFR ligands including AREG, HB-EGF and TGFα in transformed keratinocytes. Exogenous EGFR ligands recapitulate, whereas the EGFR inhibitors antagonize, the growth stimulating effect of vemurafenib. Accordingly, the compound of Formula I or Formula II, which does not induce expression of the MAPK pathway response genes, will not express EGFR ligands. Compensatory activation of EGFR and other RTKs including PDGFR, IGF-1R, and MET has been shown to cause acquired resistance to BRAF inhibition in melanoma (Nazarian 2010; Villanueva 2010; Straussman 2012). The unresponsiveness of BRAFV600E colorectal cancer to BRAF inhibitors was also attributed to feedback activation of EGFR (Corcoran 2012; Prahallad 2012). Therefore, the compound of Formula I or Formula II, can be advantageous in treating subjects with BRAF mutant carcinomas besides melanoma such as papillary thyroid cancer, colorectal cancer, and other cancers.

The compounds of Formula I and Formula II satisfy the unmet needs of the first generation of BRAF inhibitors, as demonstrated in the examples below. The examples demonstrate that Formula I inhibits mutant BRAF cells without activating the MAPK pathway in cells containing RAS mutation or receptor tyrosine kinase activation. It is also demonstrated in the examples that the compounds of Formula I and Formula II each selectively inhibits the mutated BRAF kinases including the most common—BRAFV600E—with single digit nM $IC_{50}$, while having minimal effects on the activities of other kinases. By dissociating MAPK pathway inhibition from pathway activation, the compound of Formula I has a separate and improved activity profile.

The methods and uses of the compound of Formula I or Formula II described herein is a selection invention of U.S. Patent Publication No. 2014/0128373. Specifically, the compounds of Formula I and II are each a very potent BRAF V600E mutant inhibitor and are also a particularly strong paradox breaker, wherein Formula I and II do not activate the MAPK pathway which is typical of the first generation BRAF V600E mutant inhibitors. The compound of Formula I is therefore highly advantageous in this respect, and it has been tested and proven to be potentially useful for various indications.

In a cell model that expresses the same HRAS mutation prevalent in squamous cell tumors from patients treated with RAF inhibitors, first-generation RAF inhibitors stimulate the in vitro and in vivo growth of the cells and induce the expression of MAPK pathway response genes including EGFR ligands. By contrast, the paradox breakers of Formula I and Formula II had no such effect. In addition, the compound of Formula I surprisingly overcame several known mechanisms of resistance to the first generation RAF inhibitors. Based on these advantageous properties of the compound of either Formula I or Formula II, enhanced tolerability and, in turn, increased drug dosage may be obtained.

III. Embodiments

Disclosed is a new use of a class of BRAF inhibitors, which have been found to inhibit mutant RAF cells without activating the MAPK pathway or inducing expression of MAPK pathway genes in cells harboring wild-type BRAF, at exceptional and unexpected levels, in cells containing an upstream activation event. Accordingly, the present disclosure overcomes the obstacles that are present in the first generation BRAF inhibitors that are currently in use.

Specifically, the present disclosure relates to a method of treating a subject suffering from or at risk of a BRAF V600 mutation or a BRAF fusion mutation related disease or condition without activating the MAPK pathway or inducing expression of MAPK pathway genes in cells harboring wild-type BRAF, comprising administering to the subject a therapeutically effective amount of a compound of Formula I or II:

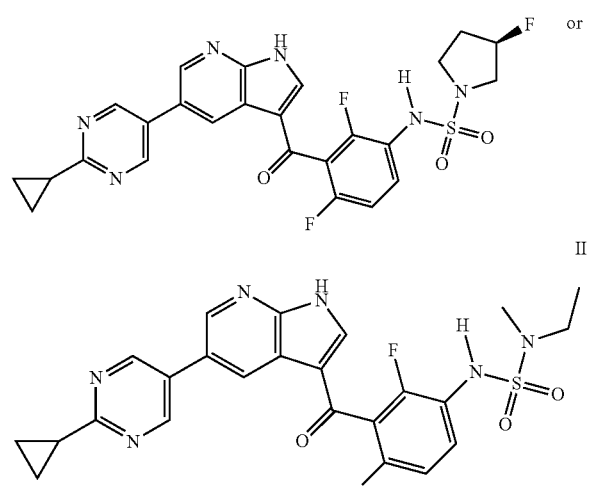

or a pharmaceutically acceptable salt, isomer, tautomer or deuterated form thereof.

The compound of Formula I (or "Formula I") is also known as (3R)—N-[3-[5-(2-cyclopropylpyrimidin-5-yl)-1H-pyrrolo[2,3-b]pyridine-3-carbonyl]-2,4-difluorophenyl]-3-fluoropyrrolidine-1-sulfonamide. The compound of Formula II (or "Formula II") is also known as 5-(2-cyclopropylpyrimidin-5-yl)-3-[3-[[ethyl(methyl)sulfamoyl]amino]-2,6-difluoro-benzoyl]-1H-pyrrolo[2,3-b]pyridine.

In some embodiments, a method of treating a subject suffering from or at risk of a BRAF V600 mutation related disease or condition without activating the MAPK pathway or inducing expression of MAPK pathway genes in cells harboring wild-type BRAF, comprises administering a compound of Formula I. In some embodiments, a method of treating a subject suffering from or at risk of a BRAF V600 mutation related disease or condition without activating the MAPK pathway or inducing expression of MAPK pathway genes in cells harboring wild-type BRAF, comprises administering a compound of Formula II.

In another embodiment, the non-activation of the MAPK pathway or non-inducement of expression of the MAPK pathway genes in cells harboring wild-type BRAF comprises inhibition of phosphor-ERK (pERK) in BRAF wild-type cells. In another embodiment, the non-activation of the MAPK pathway or non-inducement of expression of MAPK pathway genes in cells harboring wild-type BRAF comprises inhibition of pERK and pMEK in BRAF wild-type cells. In another embodiment, the non-activation of the MAPK pathway or non-inducement of expression of MAPK pathway genes in cells harboring wild-type BRAF prevents stimulation of cell growth. In another embodiment, the inhibition of pERK in BRAF wild-type cells prevents stimulation of cell growth. In another embodiment, the inhibition of pERK and pMEK in BRAF wild-type cells prevents stimulation of cell growth. In another embodiment, the non-activation of the MAPK pathway or non-inducement of expression of MAPK pathway genes in cells harboring wild-type BRAF prevents stimulation skin neoplasms. In another embodiment, the inhibition of pERK in BRAF wild-type cells prevents stimulation of skin neoplams. In another embodiment, the inhibition of pERK and pMEK in BRAF wild-type cells prevents stimulation of skin neoplasms. In another embodiment, the non-activation of the MAPK pathway or non-inducement of expression of MAPK pathway genes in cells harboring wild-type BRAF prevents stimulation of other malignancies. Non-limiting examples include leukemia or colorectal cancer.

Another embodiment of the disclosure relates to a method of treating a subject suffering from or at risk of a BRAF V600 mutation or a BRAF fusion mutation related disease or condition without activating the MAPK pathway or inducing expression of MAPK pathway genes in cells harboring wild-type BRAF, comprising administering to the subject a pharmaceutical composition comprising a therapeutically effective amount of a compound of Formula I or Formula II, or a pharmaceutically acceptable salt, isomer, tautomer or deuterated form thereof, and a pharmaceutically acceptable excipient or carrier. In another embodiment, the non-activation of the MAPK pathway or non-inducement of expression of MAPK pathway genes in cells harboring wild-type BRAF comprises inhibition of pERK in BRAF wild-type cells. In another embodiment, the non-activation of the MAPK pathway or non-inducement of expression of MAPK pathway genes in cells harboring wild-type BRAF comprises inhibition of pERK and pMEK in BRAF wild-type cells. In another embodiment, the non-activation of the MAPK pathway or non-inducement of expression of MAPK pathway genes in cells harboring wild-type BRAF prevents stimulation of cell growth. In another embodiment, the inhibition of pERK in wild-type BRAF cells prevents stimulation of cell growth. In another embodiment, the inhibition of pERK and pMEK in wild-type BRAF cells prevents stimulation of cell growth. In another embodiment, the non-activation of the MAPK pathway or non-inducement of expression of MAPK pathway genes in cells harboring wild-type BRAF prevents stimulation skin neoplasms. In another embodiment, the inhibition of pERK wild-type cells prevents stimulation of skin neoplams. In another embodiment, the inhibition of pERK and pMEK in wild-type BRAF cells prevents stimulation of skin neoplasms.

Another embodiment of the disclosure relates to a method of treating a subject suffering from or at risk of a BRAF V600 mutation or a BRAF fusion mutation related disease or condition without activating the MAPK pathway or inducing expression of MAPK pathway genes in cells harboring wild-type BRAF, comprising administering to the subject a pharmaceutical composition comprising a therapeutically effective amount of Formula I or Formula II, or a pharmaceutically acceptable salt, isomer, tautomer or deuterated form thereof, and another therapeutic agent. In another embodiment, the non-activation of the MAPK pathway or non-inducement of expression of MAPK pathway genes in cells harboring wild-type BRAF comprises inhibition of pERK in wild-type BRAF cells. In another embodiment, the non-activation of the MAPK pathway or non-inducement of expression of MAPK pathway genes in cells harboring wild-type BRAF comprises inhibition of pERK and pMEK in wild-type BRAF cells. In another embodiment, the non-activation of the MAPK pathway or non-inducement of expression of MAPK pathway genes in cells harboring wild-type BRAF prevents stimulation of cell growth. In another embodiment, the inhibition of pERK in wild-type BRAF cells prevents stimulation of cell growth. In another embodiment, the inhibition of pERK and pMEK in wild-type BRAF cells prevents stimulation of cell growth. In another embodiment, the non-activation of the MAPK pathway or non-inducement of expression of MAPK pathway genes in cells harboring wild-type BRAF prevents stimulation skin neoplasms. In another embodiment, the inhibition of pERK in BRAF wild-type cells prevents stimulation of skin neoplasms. In another embodiment, the inhibition of pERK and pMEK in wild-type BRAF cells prevents stimulation of skin neoplasms.

Non-limiting examples of BRAF V600 mutations include V600E, V600K, V600A, V600G, V600M, and V600R, with V600E and V600K being the first and second most common. In biochemical assays using recombinant enzymes, the $IC_{50}$ values ranged from 3.5 to 14.2 nM for the compound of Formula I. See Example 3 and Table 1.

Non-limiting examples of BRAF fusion mutation related diseases or conditions include pediatric astrocytomas.

The BRAF V600E mutation occurs in about half of all melanomas (Rajagopalan 2002) and in many additional cancers, as well as other types of disease or conditions. The following BRAF V600E mutation related diseases or conditions are contemplated for the methods and uses of the compound of Formula I described herein.

Non-limiting examples of BRAF V600 mutation related diseases or conditions include melanoma (including metastatic melanoma, stage 3A melanoma, stage 3B melanoma, stage 3C melanoma, and skin pigmentation melanoma), colorectal cancer (including colorectal adenocarcinoma) (Cohen 2003), papillary thyroid cancer (Fukushima 2003; Kimura 2003; Xu 2003), anaplastic thyroid cancer (Xu 2003), serous ovarian cancer (Nikiforova 2003), non-small-cell lung cancer (Singer 2003), gastric cancer (Brose 2002), cholangiocarcinoma (Lee 2003), Barrett's esophageal cancer (Tannapfel 2003), and head and neck cancers (Sommerer 2004; Weber 2003). Other non-limiting examples of BRAF V600 mutation related cancers include hepatocellular carcinoma (Colombino 2012), Langerhan's cell histiocytosis (Badalian-Very 2010), gastrointestinal stromal cell tumors (Agaram 2008), multiple myeloma (Chapman 2011), pediatric astrocytomas (which contain mostly BRAF duplications) (Jones 2008; Pfister 2008; Sievert 2009), pleomorphic xanthoastrocytomas (Dias-Santagata 2011; Schindler 2011), chronic myeloid leukemia, acute myelomonocytic leukemia, biphenotypic B myelomonocytic leukemia, acute myeloid leukemia, and hairy cell leukemia (Tiacci 2011). Other non-limiting examples of BRAF V600 mutation related cancer include periphial nerve sheath tumors, such as benign and malignant periphial nerve sheath tumors (Serrano 2013). BRAF V600 mutations are also very frequent in nevi (Pollock 2003), which are generally dysplastic lesions that derive from melanocytes and are quiescent and thus benign. BRAF V600 mutations also occurs in Erdheim-Chester disease.

Other BRAF 600V related conditions or disorders include inflammatory and autoimmune disease (such as rheumatoid arthritis) (*Mol Immunol.* 2013 October; 55(3-4):247-52), tenosynovial giant cell tumor, pigmented villonodular synovitis, giant cell tumor of tendon sheath, giant cell tumor of bone, cervical cancer (*Gynecol Oncol.* 2007 June; 105(3):662-6.), endometrial cancer (*Fam Cancer.* 2014 March; 13(1):1-12), germ cell tumors (*J Clin Oncol.* 2009 May 1; 27(13):2129-36), prostate cancer (*Genes Chromosomes Cancer.* 2012 November; 51(11):1014-23), bladder cancer (*Mol Cancer Res.* 2015 Mar. 12. pii: molcanres.0689.2014), myopericytoma (*J Natl Cancer Inst.* 2014 Jul. 25; 106(8)), metanephric adenoma (*Am J Surg Pathol.* 2015 April; 39(4):549-57), pancreatic neoplasms (*J Pathol.* 2014 March; 232(4):428-35), neuroendocrine tumors (Am J Clin Pathol. 2005 February; 123(2):256-60), endocrine tumors (*Endocr Relat Cancer.* 2004 December; 11(4):855-60), adrenal tumors (Endocr Relat Cancer. 2009 June; 16(2):565-72), adrenal medullary tumors, cystadenocarcinoma of the parotid (Springerplus. 2013 Dec. 18; 2:679. doi: 10.1186/2193-1801-2-679), glioblastoma multiforme (World J Surg Oncol. 2015 Mar. 11; 13:100), bile duct cancer including bile duct adenoma (Hepatology. 2015 January; 61(1):403-5), choloangiocarcinoma, B-cell chronic lymphoproliferative disorder (*Blood.* 2012 Jan. 5; 119(1):188-91), dendritic cell sarcomas (*Ann Diagn Pathol.* 2015 June; 19(3):113-6), histiocytic sarcomas, and lymphoma (e.g. Richter's syndrome, non-hodgkin's lymphoma) (*Cell.* 2015 Apr. 9; 161(2):319-32).

In another embodiment, the BRAF V600 mutation related disease or condition is melanoma, colorectal cancer, papillary thyroid cancer, anaplastic thyroid cancer, ovarian cancer, non-small-cell lung cancer, gastric cancer, cholangiocarcinoma, Barrett's esophageal cancer, head and neck cancer, hepatocellular carcinoma, Langerhan's cell histiocytosis, gastrointestinal stromal cell tumours, multiple myeloma, pediatric astrocytomas, pleomorphic xanthoastrocytomas, chronic myeloid leukemia, acute myelomonocytic leukemia, biphenotypic B myelomonocytic leukemia, acute myeloid leukemia, hairy cell leukemia, nevi, Erdheim-Chester disease, inflammatory and autoimmune disease (such as rheumatoid arthritis), tenosynovial giant cell tumor, pigmented villonodular synovitis, giant cell tumor of tendon sheath, giant cell tumor of bone, cervical cancer, endometrial cancer, germ cell tumors, prostate cancer, bladder cancer, myopericytoma, metanephric adenoma, pancreatic neoplasms, neuroendocrine tumors, endocrine tumors, adrenal tumors, adrenal medullary tumors, cystadenocarcinoma of the parotid, glioblastoma multiforme, bile duct cancer including bile duct adenom, choloangiocarcinoma, B-cell chronic lymphoproliferative disorder, dendritic cell sarcomas, histiocytic sarcomas, or lymphoma.

In another embodiment, the BRAF V600 mutation or a BRAF fusion mutation related disease or condition is melanoma, colorectal cancer, papillary thyroid cancer, anaplastic thyroid cancer, ovarian cancer, non-small-cell lung cancer, gastric cancer, cholangiocarcinoma, Barrett's esophageal cancer, head and neck cancer, hepatocellular carcinoma, Langerhan's cell histiocytosis, gastrointestinal stromal cell tumours, multiple myeloma, pediatric astrocytomas, pleomorphic xanthoastrocytomas, chronic myeloid leukemia, acute myelomonocytic leukemia, biphenotypic B myelomonocytic leukemia, acute myeloid leukemia, hairy cell leukemia, nevi, Erdheim-Chester disease, malignant peripheral nerve sheath tumor, inflammatory and autoimmune disease (such as rheumatoid arthritis), tenosynovial giant cell tumor, pigmented villonodular synovitis, giant cell tumor of tendon sheath, giant cell tumor of bone, cervical cancer, endometrial cancer, germ cell tumors, prostate cancer, bladder cancer, myopericytoma, metanephric adenoma, pancreatic neoplasms, neuroendocrine tumors, endocrine tumors, adrenal tumors, adrenal medullary tumors, cystadenocarcinoma of the parotid, glioblastoma multiforme, bile duct cancer including bile duct adenom, choloangiocarcinoma, B-cell chronic lymphoproliferative disorder, dendritic cell sarcomas, histiocytic sarcomas, or lymphoma.

In another embodiment, the BRAF V600 mutation related disease or condition is metastatic melanoma, colorectal cancer, papillary thyroid cancer, anaplastic thyroid cancer, ovarian cancer, non-small-cell lung cancer, gastric cancer, cholangiocarcinoma, Barrett's esophageal cancer, Erdheim-Chester disease, or head and neck cancer. In another embodiment, the BRAF V600 mutation related disease or condition is melanoma, colorectal cancer, papillary thyroid cancer, anaplastic thyroid cancer, ovarian cancer, non-small-cell lung cancer, gastric cancer, cholangiocarcinoma, Barrett's esophageal cancer, or head and neck cancer.

In another embodiment, the BRAF V600 mutation related disease or disorder is hepatocellular carcinoma, Langerhan's cell histiocytosis, gastrointestinal stromal cell tumours, multiple myeloma, pediatric astrocytomas, pleomorphic xanthoastrocytomas, chronic myeloid leukemia, acute myelomonocytic leukemia, biphenotypic B myelomonocytic leukemia, acute myeloid leukemia, hairy cell leukemia, or nevi.

In another embodiment, the BRAF V600 mutation related disease or disorder is inflammatory and autoimmune disease (such as rheumatoid arthritis), tenosynovial giant cell tumor, pigmented villonodular synovitis, giant cell tumor of tendon sheath, giant cell tumor of bone, cervical cancer, endometrial cancer, germ cell tumors, prostate cancer, bladder cancer, myopericytoma, metanephric adenoma, pancreatic neoplasms, neuroendocrine tumors, endocrine tumors, adrenal tumors, adrenal medullary tumors, cystadenocarcinoma of the parotid, glioblastoma multiforme, bile duct cancer including bile duct adenom, choloangiocarcinoma, B-cell chronic lymphoproliferative disorder, dendritic cell sarcomas, histiocytic sarcomas, or lymphoma.

In another embodiment, the BRAF V600 mutation related disease or disorder is a cancer. In another embodiment, the BRAF V600E mutation related cancer is metastatic melanoma, colorectal cancer, papillary thyroid cancer, anaplastic thyroid cancer, ovarian cancer, non-small-cell lung cancer, gastric cancer, cholangiocarcinoma, Barrett's esophageal cancer, or head and neck cancer. In another embodiment, the BRAF V600E mutation related cancer is metastatic melanoma, skin pigmentation melanoma, colorectal cancer, papillary thyroid cancer, anaplastic thyroid cancer, ovarian cancer, non-small-cell lung cancer, gastric cancer, cholangiocarcinoma, Barrett's esophageal cancer, or head and neck cancer.

In another embodiment, the BRAF V600 mutation related cancer is hepatocellular carcinoma, Langerhan's cell histiocytosis, gastrointestinal stromal cell tumours, multiple myeloma, pediatric astrocytomas, pleomorphic xanthoastrocytomas, chronic myeloid leukemia, acute myelomonocytic leukemia, biphenotypic B myelomonocytic leukemia, acute myeloid leukemia, hairy cell leukemia, or nevi.

In another embodiment, the BRAF V600 mutation related disease or condition is Erdheim-Chester disease.

In another embodiment, the BRAF V600 mutation related cancer is melanoma.

In another embodiment, the BRAF V600 mutation related cancer is metastatic melanoma.

In another embodiment, the BRAF V600 mutation related cancer is skin pigmentation melanoma.

In another embodiment, the BRAF V600 mutation related cancer is periphial nerve sheath tumors (including malignant and benign periphial nerve sheath tumors).

In another embodiment, the BRAF V600 mutation related cancer is malignant periphial nerve sheath tumors (MPNST).

In another embodiment, the BRAF V600 mutation related cancer is colorectal cancer.

In another embodiment, the BRAF V600 mutation related cancer is colorectal adenocarcinoma.

In another embodiment, the BRAF V600 mutation related cancer is papillary thyroid cancer.

In another embodiment, the BRAF V600 mutation related cancer is anaplastic thyroid cancer.

In another embodiment, the BRAF V600 mutation related cancer is ovarian cancer.

In another embodiment, the BRAF V600 mutation related cancer is non-small-cell lung cancer.

In another embodiment, the BRAF V600 mutation related cancer is gastric cancer.

In another embodiment, the BRAF V600 mutation related cancer is cholangiocarcinoma.

In another embodiment, the BRAF V600 mutation related cancer is Barrett's esophageal cancer.

In another embodiment, the BRAF V600 mutation related cancer is head and neck cancer.

In another embodiment, the BRAF V600 mutation related cancer is hepatocellular carcinoma.

In another embodiment, the BRAF V600 mutation related cancer is Langerhan's cell histiocytosis.

In another embodiment, the BRAF V600 mutation related cancer is gastrointestinal stromal cell tumours.

In another embodiment, the BRAF V600 mutation related cancer is multiple myeloma.

In another embodiment, the BRAF V600 mutation related cancer is pediatric astrocytomas.

In another embodiment, the BRAF V600 mutation related cancer is pleomorphic xanthoastrocytomas.

In another embodiment, the BRAF V600 mutation related cancer is chronic myeloid leukemia.

In another embodiment, the BRAF V600 mutation related cancer is acute myelomonocytic leukemia.

In another embodiment, the BRAF V600 mutation related cancer is biphenotypic B myelomonocytic leukemia.

In another embodiment, the BRAF V600 mutation related cancer is acute myeloid leukemia.

In another embodiment, the BRAF V600 mutation related cancer is hairy cell leukemia.

In another embodiment, the BRAF V600 mutation related cancer is nevi.

In another embodiment, the BRAF V600 mutation related disease or condition is selected from the group consisting of ischemic stroke, cerebrovascular ischemia, multi-infarct dementia, head injury, spinal cord injury, Alzheimer's disease, Parkinson's disease, amyotrophic lateral sclerosis, dementia, senile chorea, Huntington's disease, neoplastic disease, complications with neoplastic disease, chemotherapy-induced hypoxia, gastrointestinal stromal tumors, prostate tumors, mast cell tumors, canine mast cell tumors, acute myeloid leukemia, acute lymphocytic leukemia, chronic myeloid leukemia, chronic lymphocytic leukemia, multiple myeloma, melanoma, mastocytosis, glioma, glioblastoma, astrocytoma, neuroblastoma, sarcomas, sarcomas of neuroectodermal origin, leiomyosarcoma, lung carcinoma, breast carcinoma, pancreatic carcinoma, colon carcinoma, hepatocellular carcinoma, renal carcinoma, carcinoma of the female genital tract, squamous cell carcinoma, carcinoma in situ, lymphoma, histiocytic lymphoma, non-Hodgkin's lymphoma, MEN2 syndromes, neurofibromatosis, Schwann cell neoplasia, myelodysplastic syndrome, leukemia, tumor angiogenesis, thyroid cancer, liver cancer, bone cancer, skin cancer, brain cancer (including pediatric brain tumors and BRAF-fusion brain tumors), cancer of the central nervous system, pancreatic cancer, lung cancer, small cell lung cancer, non small cell lung cancer, breast cancer, colon cancer, bladder cancer, prostate cancer, gastrointestinal tract cancer, cancer of the endometrium, fallopian tube cancer, testicular cancer, ovarian cancer, pain of neuropathic origin, pain of inflammatory origin, acute pain, chronic pain, migraine, cardiovascular disease, heart failure, cardiac hypertrophy, thrombosis, thrombotic microangiopathy syndromes, atherosclerosis, reperfusion injury, ischemia, cerebrovascular ischemia, liver ischemia, inflammation, polycystic kidney disease, age-related macular degeneration, rheumatoid arthritis, allergic rhinitis, inflammatory bowel disease, ulcerative colitis, Crohn's disease, systemic lupus erythematosis, Sjogren's Syndrome, Wegener's granulomatosis, psoriasis, scleroderma, chronic thyroiditis, Grave's disease, myasthenia gravis, multiple sclerosis, osteoarthritis, endometriosis, dermal scarring, tissue scarring, vascular restenosis, fibrotic disorders, hypereosinophilia, CNS inflammation, pancreatitis, nephritis, atopic dermatitis, hepatitis, immunodeficiency diseases, severe combined immunodeficiency, organ transplant rejection, graft versus host disease, renal disease, prostatic disease, diabetic nephropathy, nephrosclerosis, glomerulonephritis, interstitial nephritis, Lupus nephritis, prostate hyperplasia, chronic renal failure, tubular necrosis, diabetes-associated renal complication, associated renal hypertrophy, type 1 diabetes, type 2 diabetes, metabolic syndrome, obesity, hepatic steatosis, insulin resistance, hyperglycemia, lipolysis obesity, infection, Helicobacter pylori infection, Influenza virus infection, fever, sepsis, pulmonary diseases, chronic obstructive pulmonary disease, acute respiratory distress syndrome, asthma, allergy, bronchitis, emphysema, pulmonary fibrosis, genetic developmental diseases, Noonan's syndrome, Crouzon syndrome, acrocephalo-syndactyly type I, Pfeiffer's syndrome, Jackson-Weiss syndrome, Costello syndrome, faciocutaneoskeletal syndrome, leopard syndrome, cardio-faciocutaneous syndrome, neural crest syndrome abnormalities causing cardiovascular, skeletal, intestinal, skin, hair or endocrine diseases, disorders of bone structure or mineralization, osteoporosis, increased risk of fracture, hypercalcemia, bone metastases, Grave's disease, Hirschsprung's disease, lymphoedema, selective T-cell defect, X-linked agammaglobulinemia, diabetic retinopathy, alopecia, erectile dysfunction, and tuberous sclerosis.

In some embodiments, the BRAF V600 mutation can be one or more BRAF V600 mutations. In some embodiments, the BRAF V600 mutation is one or more mutations selected from the group consisting of V600E, V600K, V600D, V600A, V600G, V600M, and V600R. In some embodiments, the BRAF V600 mutation comprises a V600E and a V600K mutation. In some embodiments, the BRAF V600 mutation comprises a V600E mutation. In some embodiments, the BRAF V600 mutation comprises a V600K mutation. In some embodiments, the BRAF V600 mutation comprises a V600D mutation. In some embodiments, the BRAF V600 mutation comprises a V600A mutation. In some embodiments, the BRAF V600 mutation comprises a V600G mutation. In some embodiments, the BRAF V600 mutation is a V600M mutation. In some embodiments, the BRAF V600 mutation comprises a V600R mutation.

IV. Alternative Compound Forms or Derivatives

The compound of Formula I or Formula II contemplated for use herein may exist in a number of different forms or derivatives, all within the scope of the present disclosure. Alternative forms or derivatives, include, for example, (a) tautomers, isomers (including stereoisomers and regioisomers), and racemic mixtures (b) pharmaceutically acceptable salts and (c) solid forms, including different crystal forms, polymorphic or amorphous solids, including hydrates and solvates thereof, and other forms.

A. Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, the compounds contemplated for use according to the present disclosure may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present disclosure. Unless specified to the contrary, all such stereoisomeric forms are included within the formulae provided herein.

In some embodiments, a chiral compound contemplated for use in accordance with the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

B. Pharmaceutically Acceptable Salts

Unless specified to the contrary, specification of a compound herein includes pharmaceutically acceptable salts of such compound. Thus, compounds described herein can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the disclosure may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenyl acetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see Remington's Pharmaceutical Sciences, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

C. Other Compound Forms

In the case of agents that are solids, it is understood by those skilled in the art that the compounds and salts contemplated for use in accordance with the present disclosure may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds contemplated for use according to the present disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the disclosure with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, DMSO, ethyl acetate, acetic acid, or ethanolamine.

V. Combination Therapies

In some embodiments, the disclosure provides methods of treating any of the diseases or conditions described herein in an animal subject in need thereof, wherein the method involves administering to the subject an effective amount of the compound of Formula I or II in combination with one or more other therapies for the disease or condition.

A. Formula I or II in Combination with Another Agent

In some embodiments, compounds of Formula I or Formula II, or pharmaceutical compositions comprising compounds of Formula I or Formula II, may be administered with another therapeutic agent. In some embodiments, the another therapeutic agent may be an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, pembrolizumab, nivolumab, bevacizumab, cetuximab, galiximab, gemtuzumab, panitumumab, pertuzumab, rituximab, tositumomab, trastuzumab, 90Y-ibritumomab tiuxetan, ipilimumab, and tremelinuimab; a hormone or honnone antagonist, including, but not limited to, anastrozole, androgens, buserelin, diethylstilbestrol, exemestane, flutamide, fulvestrant, goserelin, idoxifene, letrozole, leuprolide. magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, bclotecan, edotecarin, etoposide, etoposide phosphate, exatecan, irinotecan (also active metabolite SN-38 (7-ethyl-10-hydroxy-camptothecin)), lucanthone, mitoxantrone. pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapalinib, motesanib diphosphate (AMG 706), nilotinib (AMN 107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elescloniol, eribulin mesylate (E7389), ixabepilone, lonidamine, masoprocol, mitoguanazone, oblimersen, sulindac, testolactonc, tiazofurin, mTOR inhibitors (e.g. temsirolimus, everolimus, deforolimus), PI3K inhibitors (e.g. BKM120, BEZ235, GDC-0941, XL1 7, XL765), Cdk4 inhibitors (e.g. PD-332991), Akt inhibitors, Hsp90 inhibitors (e.g. tanespimycin) and famesyltransferase inhibitors (e.g. tipifarnib); EK inhibitors (e.g., AS703026, AZD6244 (selumetinib), AZD8330, BIX02188, CI 1040 (PD184352), D-87503, GS 1 120212 (JTP-74057), PD0325901, PD3 18088, PD98059, PDEA1 19 (BAY 869766), TAK-733). In another embodiment, the method of treating a cancer involves administering to the subject an effective amount of a composition including any one or more compound(s) as described herein in combination with a chemotherapeutic agent selected from capecitabine, 5-fluorouraeil, carboplatin, dacarbazine, gefitinib, oxaliplatin, paclitaxel, SN-38, temozolomide, vinblastine, bevacizumab, cetuximab, interferon-a, interleukin-2, or erlotinib.

In some embodiments, the another therapeutic agent may be one or more of the following agents: a adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, uramustine, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, zorubicin, aminopterin, azacitidine, azathioprine, capecitabine, cladribine, clofarabine, cytarabine, decitabine, floxuridine, fludarabinc, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, vidarabine, alemtuzumab, pembrolizumab, nivolumab, bevacizumab, cetuximab, galiximab, gemtuzumab, panitumumab, pertuzumab, rituximab, tositumomab, trastuzumab, 90Y-ibritumomab tiuxetan, ipilimumab, tremelinuimab, anastrozole, androgens, buserelin, diethylstilbestrol, exemestane, flutamide, fulvestrant, goserelin, idoxifene, letrozole, leuprolide. magestrol, raloxifene, tamoxifen, toremifene, DJ-927, docetaxel, TPI 287, larotaxel, ortataxel, paclitaxel, DHA-paclitaxel, tesetaxel, alitretinoin, bexarotene, fenretinide, isotretinoin, tretinoin, demecolcine, homoharringtonine, vinblastine, vincristine, vindesine, vinflunine, vinorelbine, an antiangiogenic agent, including, but not limited to, Neovastat, ABT-510, 2-methoxyestradiol, lenalidomide, thalidomide, amsacrine, edotecarin, etoposide, etoposide phosphate, exatecan, irinotecan, lucanthone, mitoxantrone. pixantrone, rubitecan, teniposide, topotecan, 9-aminocamptothecin, axitinib, erlotinib, gefitinib, flavopiridol, imatinib mesylate, cabozantinib, lapalinib, motesanib diphosphate, nilotinib, seliciclib, sorafenib, sunitinib malate, AEE-788, BMS-599626, 7-hydroxystaurosporine, vatalanib, bortezomib, geldanamycin, rapamycin, imiquimod, interferon-α, interleukin-2, 3-amino-2-carboxyaldehyde thiosemicarbazone, altrasentan, aminoglutethimide, anagrelide, asparaginase, bryostatin-1, cilengitide, elescloniol, eribulin mesylate, ixabepilone, lonidamine, masoprocol, mitoguanazone, oblimersen, sulindac, testolactone, tiazofurin, temsirolimus, everolimus, deforolimus, a PI3K inhibitor, a Cdk4 inhibitor, a Akt inhibitor, a Hsp90 inhibitor, an EGFR inhibitor, an IDO inhibitor, a farnesyltransferase inhibitor, a MEK inhibitor, a BET inhibitor, AS703026, selumetinib, AZD8330, BIX02188, PD184352, D-87503, GS 1 120212, PD0325901, PD3 18088, PD98059, PDEA1 19, or TAK-733.

In another aspect, the disclosure provides a method for treating a cancer in a subject in need thereof by administering to the subject an effective amount of the compound of Formula I or II with one or more suitable chemotherapeutic agents. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy including indoleamine 2,3-dioxygenase (IDO) inhibitors, an antibody therapy, including, but not limited to immune checkpoint inhibitors such as PD-1 inhibitors (such as pembrolizumab, nivolumab, pidilizumab) or PD-L1 inhibitors (such as BMS-936559, MEDI4736, MPDL3280A, or MSB0010718C), alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, cabozantinib, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, and vatalanib; a targeted signal transduction inhibitor including, but not limited to bortezomib, geldanamycin, and rapamycin; a biological response modifier, including, but not limited to, imiquimod, interferon-γ, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. INK28, AZD8055, sirolimus, temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib), and Aromatase inhibitors (anastrozole letrozole exemestane). In another embodiment of the methods and uses described herein, the compound of Formula I or II is administered in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In another embodiment, the chemotherapeutic agent is a Mek inhibitor. Exemplary Mek inhibitors include, but are not limited to trametinib, cobimetinib, AS703026, AZD6244 (Selumetinib), AZD8330, BIX 02188, CI-1040 (PD184352), GSK1120212 (JTP-74057), PD0325901, PD318088, PD98059, RDEA119(BAY 869766), TAK-733 and U0126-EtOH. In another embodiment, the chemotherapeutic agent is a tyrosine kinase inhibitor. Exemplary tyrosine kinase inhibitors include, but are not limited to, AEE788, AG-1478 (Tyrphostin AG-1478), AG-490, Apatinib (YN968D1), AV-412, AV-951(Tivozanib), Axitinib, AZD8931, BIBF1120 (Vargatef), BIBW2992 (Afatinib), BMS794833, BMS-599626, Brivanib (BMS-540215), Brivanib alaninate (BMS-582664), Cediranib (AZD2171), Chrysophanic acid (Chrysophanol), Crenolanib (CP-868569), CUDC-101, CYC116, Dovitinib Dilactic acid (TKI258 Dilactic acid), E7080, Erlotinib Hydrochloride (Tarceva, CP-358774, OSI-774, NSC-718781), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib (TAK 165), Neratinib (HKI-272), NVP-BHG712, OSI-420 (Desmethyl Erlotinib, CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, Cabozantinib, XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), and DPP4 inhibitors (sitagliptin, vildagliptin, saxagliptin, dutogliptin, gemigliptin, alogliptin). In another embodiment, the agent is a BET inhibitor (such as BRD2, BRD3, BRD4 and/or BRDT). In another embodiment, the agent is an EGFR inhibitor. Exemplary EGFR inhibitors include, but are not limited to, AEE-788, AP-26113, BIBW-2992 (Tovok), CI-1033, GW-572016, Iressa, LY2874455, RO-5323441, Tarceva (Erlotinib, OSI-774), CUDC-101, cetuximab and WZ4002. In another embodiment, the disclosure provides a method for treating a cancer in a subject in need thereof by administering to the subject an effective amount of the compound of Formula I or II with a topoisomerase inhibitor (such as irinotecan) and an EGFR inhibitor (such as cetuximab).

In some embodiments, the another therapeutic agent may be one or more of the following agents: adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, uramustine, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, zorubicin, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, vidarabine, an (IDO) inhibitors, a PD-1 inhibitor, a PD-L1 inhibitor, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab, an anti-CTLA-4 antibody, anastrozole, androgens, buserelin, diethylstilbestrol, exemestane, flutamide, fulvestrant, goserelin, idoxifene, letrozole, leuprolide, magestrol, raloxifene, tamoxifen, toremifene, a taxane, a retinoid, an alkaloid, an antiangiogenic agent, a topoisomerase inhibitor, axitinib, dasatinib, erlotinib, gefitinib, flavopiridol, imatinib mesylate, lapatinib, motesanib diphosphate, nilotinib, seliciclib, sorafenib, sunitinib malate, AEE-788, BMS-599626, 7-hydroxystaurosporine, vemurafenib, dabrafenib, selumetinib, vatalanib, bortezomib, geldanamycin, rapamycin, imiquimod, interferon-γ, interleukin-2, 3-amino-2-carboxyaldehyde thiosemicarbazone, altrasentan, aminoglutethimide, anagrelide, asparaginase, bryostatin-1, cilengitide, elesclomol, eribulin mesylate, ixabepilone, lonidamine, masoprocol, mitoguanazone, oblimersen, sulindac, testolactone, tiazofurin, INK28, AZD8055, sirolimus, temsirolimus, everolimus, deforolimus, BEZ235, GDC-0941, XL147, XL765, PD-332991, an Akt inhibitor, geldanamycin, radicicol, tanespimycin, tipifarnib, anastrozole letrozole exemestane, trametinib, cobimetinib, AS703026, selumetinib, AZD8330, BIX 02188, PD184352, GSK1120212, PD0325901, PD318088, PD98059, BAY 869766, TAK-733, U0126-EtOH, AEE788, tyrphostin, AG-490, apatinib, AV-412, tivozanib, axitinib, AZD8931, vargatef, afatinib, BMS794833, BMS-599626, brivanib, brivanib alaninate, cediranib, chrysophanic acid, crenolanib, CUDC-101, CYC116, dovitinib dilactic acid, E7080, erlotinib hydrochloride, foretinib, gefitinib, imatinib, imatinib mesylate, Ki8751, KRN 633, lapatinib, linifanib, masitinib, MGCD-265, Motesanib, MP-470, mubritinib, neratinib, NVP-BHG712, desmethyl erlotinib, OSI-930, pazopanib HCl, PD-153035 HCl, PD173074, pelitinib, PF299804, ponatinib, PP121, RAF265, regorafenib, sorafenib tosylate, sunitinib malate, telatinib, TSU-68, vandetanib, vatalanib dihydrochloride, WZ3146, WZ4002, WZ8040, cabozantinib, XL647, EGFR siRNA, FLT4 siRNA, KDR siRNA, an antidiabetic agent, a PPAR agonist, a DPP4 inhibitor, a BET inhibitor or an EGFR inhibitor.

In some embodiments, the another therapeutic agent may be a bromodomain inhibitor. Inhibitors of bromodomains (e.g., BET proteins, such as BRD2, BRD3, BRD4, and/or BRDT), can be useful for the treatment of diseases related to abnormal expression of bromodomains, including cell proliferative disorders, cancers, chronic autoimmune, inflammatory conditions, among others. Non-limiting examples of BET inhibitors include GSK1210151A and GSK525762.

In some embodiments, the another therapeutic agent may be a histone deacetylase inhibitor. The histone deacetylase inhibitors (HDAC inhibitors) are cytostatic agents that inhibit the proliferation of tumor cells in culture and in vivo by inducing cell cycle arrest, differentiation and/or apoptosis. HDAC inhibitors exert their anti-tumor effects via the induction of expression changes of oncogenes or tumour suppressor, through modulating that the acetylation/deactylation of histones and/or non-histone proteins such as transcription factors. Histone acetylation and deacetylation play important roles in the modulation of chromatin topology and the regulation of gene transcription. Non-limiting examples of HDAC inhibitors include vorinostat, romidepsin, chidamide, panobinostat, belinostat, valproic acid, mocetinostat, abexinostat, entinostat, resminostat, givinostat, and quisinostat. HDAC inhibitors have been used extensively in psychiatry and neurology as mood stabilzers and anti-epileptics. One example of this is valproic acid, marketed as a drug under the trade names Depakene, Depakote, and Divalproex. HDAC inhibitors are also being used as a mitigator for neurodegenerative diseases such as Alzheimer's disease and Huntington's disease.

B. Formula I or II in Combination with Another Therapy

In some embodiments, the disclosure provides a method of treating a cancer in a subject in need thereof by administering to the subject an effective amount of the compound of Formula I or II, or a composition thereof, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), oncolytic viral or bacterial therapy, surgery, or bone marrow and stem cell transplantation. In certain embodiments, the disclosure provides a method of treating a cancer in a subject in need thereof by administering to the subject an effective amount of a compound of Formula I or Formula II described herein and applying a radiation treatment as described herein either separately or simultaneously. In one embodiment, the disclosure provides a method for treating a cancer in a subject in need thereof by administering an effective amount of a compound of Formula I or Formula II described herein to the subject followed by a radiation treatment (e.g. x-ray, γ-ray, or electron, proton, neutron, or α particle beam). In another embodiment, the disclosure provides a method for treating a cancer in a subject in need thereof by applying a radiation treatment (e.g. x-ray, γ-ray, or electron, proton, neutron, or a particle beam) to the subject followed by administering an effective amount of Formula I or Formula II described herein to the subject. In yet another embodiment, the disclosure provides a method for treating a cancer in a subject in need thereof by administering a compound of Formula I or Formula II described herein and a radiation therapy (e.g. x-ray, γ-ray, or electron, proton, neutron, or α particle beam) to the subject simultaneously.

VI. Kits

In another aspect, the disclosure provides kits that include a compound of Formula I or II, or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a BRAF protein kinase mediated disease or condition; the disclosure kit includes written instructions for use and/or other indication that the compound or composition is suitable or approved for administration to a mammal, e.g., a human, for a BRAF protein kinase-mediated disease or condition; and the compound or composition is packaged in unit dose or single dose form, e.g., single dose pills, capsules, or the like.

VII. Formulations and Administration

The methods and uses described herein will typically be used in therapy for human subjects. However, they may also be used to treat similar or identical indications in other animal subjects. Compounds of Formula I or Formula II described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

In some embodiments, compositions used in the methods of the present disclosure will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium tri silicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 400 or PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds of Formula I or II described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, active components, such as compounds of Formula I or Formula II, may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds of Formula I or II described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, compounds of Formula I or II described herein may be formulated in solid form, including, for example, lyophilized forms, and redissolved or suspended prior to use.

In some embodiments, transmucosal, topical or transdermal administration may be used. In such formulations of compounds of Formula I or Formula II described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds of Formula I or Formula II described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds of Formula I or II, or compositions thereof, is administered as an inhalant. Compounds of Formula I or II described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. Compounds of Formula I or Formula II described herein may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of Formula I or II to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

Compounds of Formula I or II described herein may also be used in combination with other therapies for treating the same disease. Such combination use includes administration of compounds of Formula I or Formula II, and one or more other therapeutics at different times, or co-administration of compounds of Formula I or Formula II, and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

The compound of Formula I or II, or a pharmaceutically acceptable salt, isomer, tautomer or deuterated form thereof, may be used in combination with another chemotherapeutic agent or drug or a kinase inhibitor as described herein for treating the same disease. Such combination can be a fixed dose composition or be administered at different times, or co-administration of a compound of Formula I or II and another agent, drug or kinase inhibitor can be simultaneously or separately. In some embodiments, dosage may be modified for compounds of Formula I or II disclosed herein or another agent, drug or kinase inhibitor used in combination, e.g., reduction or increase in the amount dosed relative to a compound used alone to improve safety and/or efficacy, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks) than compounds of Formula I or Formula II described herein, or at the same time as compounds of Formula I or II described herein. Use in combination also includes use with a therapy or medical procedure that is administered once or infrequently, such as surgery, along with compounds of Formula I or Formula II described herein administered within a short time or longer time before or after the other therapy or procedure. In some embodiments, the present disclosure provides for delivery of compounds of Formula I or II described herein and one or more other drug therapeutics delivered by a different route of administration or by the same route of administration. The use in combination for any route of administration includes delivery of compounds of Formula I or Formula II described herein and one or more other drug therapeutics delivered by the same route of administration together in any formulation, including formulations where the two compounds are chemically linked in such a way that they maintain their therapeutic activity when administered. In one aspect, the other drug therapy may be co-administered with compounds of Formula I or Formula II described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes.

Co-administration of separate formulations includes co-administration by delivery via one device, for example the same inhalant device, the same syringe, etc., or administration from separate devices within a short time of each other. Co-formulations of compounds of Formula I or II described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

VIII. References

Agaram, N. P. et al. Novel V600E BRAF mutations in imatinib-naive and imatinib-resistant gastrointestinal stromal tumors. *Genes Chromosomes Cancer* 47, 853-859 (2008).

Anforth R M, Blumetti T C M P, Kefford R F, Sharma R, Scolyer R a, Kossard S, et al. Cutaneous manifestations of dabrafenib (GSK2118436): a selective inhibitor of mutant BRAF in patients with metastatic melanoma. Br. J. Dermatol. 2012 November; 167(5): 1153-1160.

Badalian-Very, G. et al. Recurrent BRAF mutations in Langerhans cell histiocytosis. *Blood* 116, 1919-1923 (2010).

Bollag G, Hirth P, Tsai J, Zhang J, Ibrahim P N, Cho H, et al. Clinical efficacy of a RAF inhibitor needs broad target blockade in BRAF-mutant melanoma. Nature, 2010 Sep. 30; 467(7315):596-599.

Brose, M. S. et al. BRAF and RAS mutations in human lung cancer and melanoma. *Cancer Res.* 62, 6997-7000 (2002).

Callahan M K, Rampal R, Harding J J, Klimek V M, Chung Y R, Merghoub T, et al. Progression of RAS-mutant leukemia during RAF inhibitor treatment. N. Engl. J. Med. 2012 Dec. 13; 367(24):2316-2321.

Chapman, M. A. et al. Initial genome sequencing and analysis of multiple myeloma. *Nature* 471, 467-472 (2011).

Chapman P B, Hauschild A, Robert C, Haanen J B, Ascierto P, Larkin J, et al. for BRIM-3 Study Group. Improved survival with vemurafenib in melanoma with BRAF V600E mutation. N Engl J Med. 2011 Jun. 30; 364(26): 2507-2516.

Cohen, Y. et al. BRAF mutation in papillary thyroid carcinoma. *J. Natl Cancer Inst.* 95, 625-627 (2003).

Colombino, M. et al. BRAF and PIK3CA genes are somatically mutated in hepatocellular carcinoma among patients from South Italy. *Cell Death Dis.* 3, e259 (2012).

Corcoran R B, Ebi H, Turke A B, Coffee E M, Nishino M, Cogdill A P, et al. EGFR-mediated re-activation of MAPK signaling contributes to insensitivity of BRAF mutant colorectal cancers to RAF inhibition with vemurafenib. Cancer Discov. 2012 March; 2(3):227-235.

Davies H, Bignell G R, Cox C, Stephens P, Edkins S, Clegg S, et al. Mutations of the BRAF gene in human cancer. Nature. 2002 Jun. 27; 417(6892):949-954.

Dias-Santagata, D. et al. BRAF V600E mutations are common in pleomorphic xanthoastrocytoma: diagnostic and therapeutic implications. *PLoS ONE* 6, e17948 (2011).

Flaherty K T, Puzanov I, Kim K B, Ribas A, McArthur G A, Sosman J A, et al. Inhibition of mutated, activated BRAF in metastatic melanoma. N. Engl. J. Med. 2010 Aug. 26; 363(9):809-819.

Fukushima, T. et al. BRAF mutations in papillary carcinomas of the thyroid. *Oncogene* 22, 6455-6457 (2003).

Hatzivassiliou G, Song K, Yen I, Brandhuber B J, Anderson D J, Alvarado R, et al. RAF inhibitors prime wild-type RAF to activate the MAPK pathway and enhance growth. Nature. Nature Publishing Group; 2010 Mar. 18; 464 (7287):431-435.

Hauschild A, Grob J-J, Demidov L V, Jouary T, Gutzmer R, Millward M, et al. Dabrafenib in BRAF-mutated metastatic melanoma: a multicentre, open-label, phase 3 randomised controlled trial. Lancet. Elsevier Ltd; 2012 Jul. 28; 380(9839):358-365.

Heidorn S J, Milagre C, Whittaker S, Nourry A, Niculescu-Duvas I, Dhomen N, et al. Kinase-dead BRAF and oncogenic RAS cooperate to drive tumor progression through CRAF. Cell. Elsevier Ltd; 2010 Jan. 22; 140(2): 209-221.

Huang V, Hepper D, Anadkat M, Cornelius L. Cutaneous toxic effects associated with vemurafenib and inhibition of the BRAF pathway. Arch. Dermatol. 2012 May; 148 (5):628-633.

Jones, D. T. et al. Tandem duplication producing a novel oncogenic BRAF fusion gene defines the majority of pilocytic astrocytomas. *Cancer Res.* 68, 8673-8677 (2008).

Kimura, E. T. et al. High prevalence of BRAF mutations in thyroid cancer: genetic evidence for constitutive activation of the RET/PTC-RAS-BRAF signaling pathway in papillary thyroid carcinoma. *Cancer Res.* 63, 1454-1457 (2003).

Lacouture M E, Desai a, Soltani K, Petronic-Rosic V, Laumann a E, Ratain M J, et al. Inflammation of actinic keratoses subsequent to therapy with sorafenib, a multi-targeted tyrosine-kinase inhibitor. Clin. Exp. Dermatol. 2006 November; 31(6):783-785.

Lee, S. H. et al. BRAF and KRAS mutations in stomach cancer. *Oncogene* 22, 6942-6945 (2003).

Nazarian R, Shi H, Wang Q, Kong X, Koya R C, Lee H, et al. Melanomas acquire resistance to B-RAF(V600E) inhibition by RTK or N-RAS upregulation. Nature, 2010 Dec. 16; 468(7326):973-977.

Nikiforova, M. N. et al. BRAF mutations in thyroid tumors are restricted to papillary carcinomas and anaplastic or poorly differentiated carcinomas arising from papillary carcinomas. *J. Clin. Endocrinol. Metab.* 88, 5399-5404 (2003).

Oberholzer P a, Kee D, Dziunycz P, Sucker A, Kamsukom N, Jones R, et al. RAS mutations are associated with the development of cutaneous squamous cell tumors in patients treated with RAF inhibitors. J. Clin. Oncol. 2012 Jan. 20; 30(3):316-321.

Pfister, S. et al. BRAF gene duplication constitutes a mechanism of MAPK pathway activation in low-grade astrocytomas. *J. Clin. Invest.* 118, 1739-1749 (2008).

Pollock, P. M. et al. High frequency of BRAF mutations in nevi. *Nature Genet.* 33, 19-20 (2003).

Poulikakos P I, Persaud Y, Janakiraman M, Kong X, Ng C, Moriceau G, et al. RAF inhibitor resistance is mediated by dimerization of aberrantly spliced BRAF(V600E). Nature. Nature Publishing Group; 2011 Dec. 15; 480 (7377):387-390.

Poulikakos P I, Zhang C, Bollag G, Shokat K M, Rosen N. RAF inhibitors transactivate RAF dimers and ERK signalling in cells with wild-type BRAF. Nature. Nature Publishing Group; 2010 Mar. 18; 464(7287):427-430.

Prahallad A, Sun C, Huang S, Di Nicolantonio F, Salazar R, Zecchin D, et al. Unresponsiveness of colon cancer to BRAF(V600E) inhibition through feedback activation of EGFR. Nature. 2012 Mar. 1; 483(7387):100-103.

Rajagopalan, H. et al. Tumorigenesis: RAF/RAS oncogenes and mismatch-repair status. *Nature* 418, 934 (2002).

Robert C, Arnault J-P, Mateus C. RAF inhibition and induction of cutaneous squamous cell carcinoma. Curr. Opin. Oncol. 2011 March; 23(2):177-182.

Schindler, G. et al. Analysis of BRAF V600E mutation in 1,320 nervous system tumors reveals high mutation frequencies in pleomorphic xanthoastrocytoma, ganglioglioma and extra-cerebellar pilocytic astrocytoma. *Acta Neuropathol.* 121, 397-405 (2011).

Serrano C, et al. BRAF V600E and KRAS G12S mutations in peripheral nerve sheath tumours. *Histopathology*, 2013 February; 62(3):499-504.

Sievert, A. J. et al. Duplication of 7q34 in pediatric low-grade astrocytomas detected by high-density single-nucleotide polymorphism-based genotype arrays results in a novel BRAF fusion gene. *Brain Pathol.* 19, 449-458 (2009).

Singer, G. et al. Mutations in BRAF and KRAS characterize the development of low-grade ovarian serous carcinoma. *J. Natl Cancer Inst.* 95, 484-486 (2003).

Sommerer, F. et al. Mutations of BRAF and KRAS2 in the development of Barrett's adenocarcinoma. *Oncogene* 23, 554-558 (2004).

Sosman J A, Kim K B, Schuchter L, Gonzalez R, Pavlick A C, Weber J S, et al. Survival in BRAF V600-mutant advanced melanoma treated with vemurafenib. N. Engl. J. Med. 2012 Feb. 23; 366(8):707-714.

Stellwagen J C, Adjabeng G M, Arnone M R, Dickerson S H, Han C, Hornberger K R, et al. Development of potent B-RafV600E inhibitors containing an arylsulfonamide headgroup. Bioorg. Med. Chem. Lett. Elsevier Ltd; 2011 Aug. 1; 21(15):4436-4440.

Straussman R, Morikawa T, Shee K, Barzily-Rokni M, Qian Z R, Du J, et al. Tumour micro-n environment elicits innate resistance to RAF inhibitors through HGF secretion. Nature. 2012 487:500-504.

Su, F., Viros, A., Milagre, C., Trunzer, K., Bollag, G., Spleiss, O., Reis-Filho, J. S., et al. (2012). RAS mutations in cutaneous squamous-cell carcinomas in patients treated with BRAF inhibitors. The New England journal of medicine, 366(3), 207-15.

Tannapfel, A. et al. Mutations of the BRAF gene in cholangiocarcinoma but not in hepatocellular carcinoma. *Gut* 52, 706-712 (2003).

Tiacci, E. et al. BRAF mutations in hairy-cell leukemia. *N. Engl. J. Med.* 364, 2305-2315 (2011).

Tsai, J., Lee, J. T., Wang, W., Zhang, J., Cho, H., Mamo, S., Bremer, R., et al. (2008). Discovery of a selective inhibitor of oncogenic B-Raf kinase with potent antimelanoma activity. Proceedings of the National Academy of Sciences of the United States of America, 105(8), 3041-6.

Villanueva J, Vultur A, Lee J T, Somasundaram R, Fukunaga-Kalabis M, Cipolla A K, et al. Acquired resistance to BRAF inhibitors mediated by a RAF kinase switch in melanoma can be overcome by cotargeting MEK and IGF-1R/PI3K. Cancer Cell. Elsevier Inc.; 2010 Dec. 14; 18(6):683-695.

Weber, A. et al. Mutations of the BRAF gene in squamous cell carcinoma of the head and neck. *Oncogene* 22, 4757-4759 (2003).

Xu, X., Quiros, R. M., Gattuso, P., Ain, K. B. & Prinz, R. A. High prevalence of BRAF gene mutation in papillary thyroid carcinomas and thyroid tumor cell lines. *Cancer Res.* 63, 4561-4567 (2003).

Zimmer L, Hillen U, Livingstone E, Lacouture M E, Busam K, Carvajal R D, et al. A typical melanocytic proliferations and new primary melanomas in patients with advanced melanoma undergoing selective BRAF inhibition. J Clin Oncol. 2012 30:2375-2383.

EXAMPLES

Examples related to the present disclosure are described below. In most cases, alternative techniques can be used. The examples are intended to be illustrative and are not limiting or restrictive to the scope of the disclosure.

Example 1: Compounds of Formula I and Formula II do not Activate pERK in RAS Mutant Cell Lines Compared to Vemurafenib and Dabrafenib Compounds, including vemurafenib, a compound of Formula I, and a compound of Formula II, were screened against a panel of cell lines for compound-induced change in phospho-ERK1/2 (T202/Y204, pERK). For each compound, the dissociation of pERK inhibition from activation (dubbed "ERK pathway inhibition index" or "EPII") was expressed as the ratio between the compound's mean pERK activation $EC_{50}$ in three RAS mutant cell lines (murine cuSCC cell line B9, human melanoma cell line IPC-298, and human colorectal carcinoma cell line HCT116, Table 1), and the compound's mean pERK inhibition IC$_{50}$ in two BRAF$^{V600E}$ melanoma cell lines (A375 and COLO829, Table 1).

The EPIIs for vemurafenib and dabrafenib were 11 and 4, respectively. Compounds of Formula I and Formula II potently inhibited pERK in BRAF$^{V600E}$ cells but showed essentially no pERK activation in RAS mutant cell lines at the concentrations tested (Table 1 and FIG. 1(B)). The compound of Formula II was also evaluated in the human SCC cell line A431 and the human breast adenocarcinoma cell line SKBR3 as these cells achieve MAPK pathway activation by upstream signals feeding into RAS (through over-expression of EGFR and HER2, respectively). Unlike vemurafenib, the compound of Formula II did not increase pERK levels in these cells.

1. In Vitro and In Vivo Studies

A. Biochemical Assays and Kinome Selectivity Profiling

The in vitro RAF kinase activities were determined by measuring phosphorylation of a biotinylated substrate peptide as described in Tsai et al 2008. Formula II was tested against a panel of 287 kinases at concentrations of 1 µM in duplicate. Kinases inhibited by over 50% were followed up by IC$_{50}$ determination. The 287 kinases represent all major branches of the kinome phylogenetic tree. The inhibition screen of 287 kinases was carried out under contract as complementary panels at Invitrogen (Life Technologies, WI, USA) SelectScreen™ profiling service, DiscoverX (CA, USA) KINOMEScan™ service, and Reaction Biology Corporation (PA, USA) Kinase HotSpot$^{SM}$ service.

B. Cell Culture, pERK Assay, Growth Inhibition, and EGFR Signaling Assay

The B9 cell line was obtained from Allan Balmain (University of California, San Francisco, Calif., USA). The SK-MEL-239 and SK-MEL-239-C3 cell lines were obtained from David Solit and Neal Rosen (Memorial Sloan-Kettering Cancer Center, New York, N.Y., USA). The IPC-298 cell line was obtained from DSMZ (Braunschweig, Germany). All other cell lines were obtained from ATCC. Compound dilutions were done in 100% dimethylsulfoxide ("DMSO"), and these titrations were diluted 500 fold in culture medium when added to cells resulting is a final 0.2% DMSO concentration.

Phospho-ERK AlphaScreen® assay: The degree of ERK phosphorylation was determined using an AlphaScreen® assay where an increase in ERK1/2 phosphorylation at Thr202/Tyr204 brought the donor and acceptor AlphaScreen® beads into close proximity, generating a signal for quantification. To determine the effects of compound treatment on phosphorylation of ERK1/2, cells were plated in a 96-well plate and treated with an 8-point titration of compound for one hour at 37° C. before lysis. To detect pERK, cell lysates were incubated with streptavidin-coated AlphaScreen® donor beads, anti-mouse IgG AlphaScreen® acceptor beads, a biotinylated anti-ERK1/2 rabbit antibody, and a mouse antibody that recognizes ERK1/2 only when it is phosphorylated on Thr202 and Tyr204. The biotinylated ERK1/2 antibody binds to both the streptavidin-coated AlphaScreen® donor beads and to ERK1/2 (regardless of its phosphorylation state), and the phospho-ERK1/2 antibody binds to the acceptor beads and to ERK1/2 that is phosphorylated at Thr202/Tyr204. An increase in ERK1/2 phosphorylation at Thr202/Tyr204 brings the donor and acceptor AlphaScreen® beads into close proximity, generating a signal that can be quantified on an EnVision reader (Perkin Elmer). Inhibition of ERK phosphorylation results in a loss of signal compared to DMSO controls.

Phospho-ERK immunoblot analysis: Western blots were performed by standard techniques and analyzed on an Odyssey Infrared Scanner (Li-COR Biosciences). The following antibodies were used: pERK1/2 (T202/Y204) and ERK1/2 (Cell Signaling).

Growth inhibition assay: Cells were plated into a 96-well plate at a density of 3000 cells per well and allowed to adhere overnight. Compounds were dissolved in DMSO, diluted 3-fold to create an 8-point titration and added to cells. After a 72-hour incubation, cell viability was examined using CellTiter-Glo® (Promega).

Formula II inhibited the in vitro growth of two aforementioned melanoma cell lines (A375 and COLO829) and an additional human colorectal cancer cell line COLO205 that expresses BRAF$^{V600E}$ with IC$_{50}$s 0.17 µM, 0.53 µM, and 0.16 µM, respectively, on par with vemurafenib IC$_{50}$s in the same assays (0.33 µM, 0.69 µM, and 0.25 µM, respectively).

TABLE 1

Comparison of the in vitro profile[a] of first generation BRAF inhibitors with a Paradox Breaker.

| Compound | Biochemical IC$_{50}$ (µM) | | | pERK inhibition IC$_{50}$ (µM) | | pERK activation EC$_{50}$ (µM)[b] | | | EPII[c] |
|---|---|---|---|---|---|---|---|---|---|
| | BRAF$^{V600E}$ | BRAF | CRAF | A375 | COLO829 | B9 | IPC298 | HCT116 | |
| Vemurafenib | 0.031 (±0.004) | 0.1 (±0.02) | 0.048 (±0.004) | 0.032 (±0.007) | 0.041 (±0.008) | 0.36 (±0.08) | 0.54 (±0.12) | 0.34 (±0.07) | 11 |
| Formula I | 0.0042 (±0.0006) | 0.14 (±0.02) | 0.091 (±0.014) | 0.016 (±0.005) | 0.018 (±0.005) | >200 | >200 | >200 | >10,000 |
| Formula II | 0.0038 (±0.0016) | 0.014 (±0.004) | 0.023 (±0.04) | 0.0035 (±0.0012) | 0.0021 (±0.0012) | >200 | >200 | >200 | >50,000 |
| Sorafenib | 0.35 (±0.04) | 0.072 (±0.008) | 0.011 (±0.002) | 4.4 (±1.3) | 2 (±1.2) | 0.025 (±0.005) | 0.019 (±0.01) | 0.086 (±0.04) | 0.01 |
| Dabrafenib | 0.0054 (±0.0015) | 0.0027 (±0.001) | 0.0015 (±0.001) | 0.001 (±0.001) | 0.005 (±0.003) | 0.01 [d](±0.005) | 0.01 [d](±0.005) | 0.003 (±0.002) | ~4 |

[a]Mutational status of the cell lines: A375, BRAF$^{V600E}$, homozygous; COLO829, BRAF$^{V600E}$, heterozygous; B9, HRAS$^{Q61L}$; IPC-298, NRAS$^{Q61L}$; HCT116, KRAS$^{G13D}$. Each value is an average of more than 4 experiments. Values in parenthesis indicate standard errors.
[b]EC$_{50}$, the concentration increasing pERK to 50% compared to the positive control, 10 µM PLX4720 (CAS No. 918505-84-7).
[c]ERK pathway inhibition index (EPII), the ratio between mean pERK activation EC$_{50}$ and mean pERK inhibition IC$_{50}$.
[d]Using the rising portion of the concentration-response curve As shown in FIG. 1(A), Formula II (filled in circle; bottom line) and vemurafenib (open circle; dashed top line) show similar potency to block pERK signaling in human BRAF$^{V600E}$ melanoma cell COLO829.

Figure 1B:
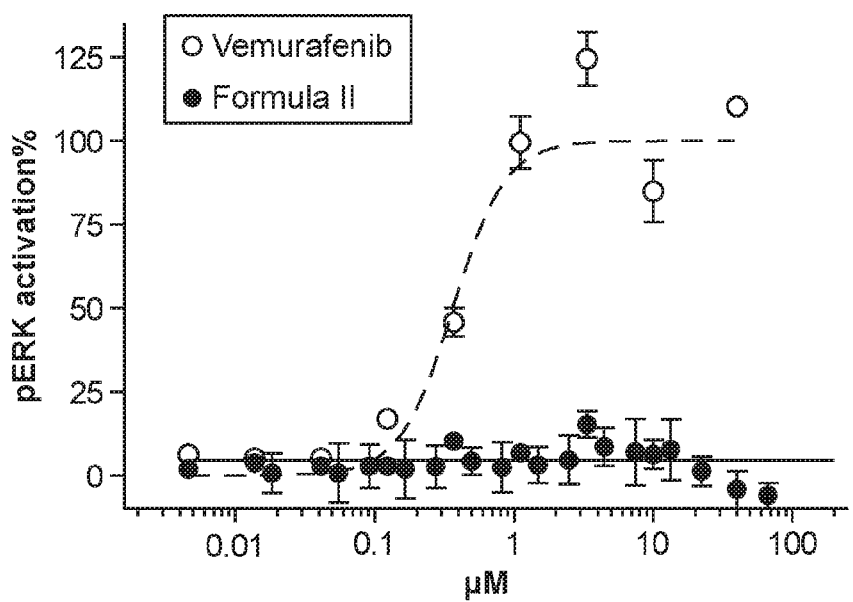
FIG. 1(B) shows that in RAS activated human melanoma cell line IPC-298 (NRAS$^{Q61L}$), vemurafenib (open circle) paradoxically activates MAPK signaling while Formula II (filled in circle) causes negligible pERK increase.
Figure 2A:
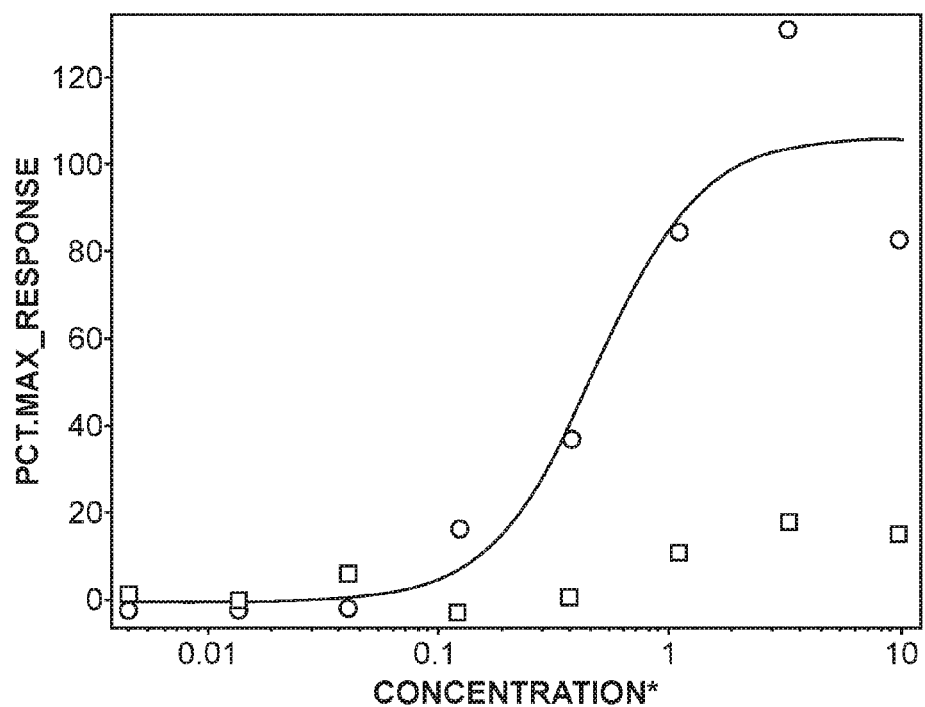
FIG. 2(A) shows that Formula I (squares) does not activate pERK in B9 cell lines in comparison to vemurafenib (circles shown with line). Vemurafenib Mean EC$_{50}$=0.56 µM (n=26); Formula I Mean EC$_{50}$=10 µM (n=14).
Figure 2B:
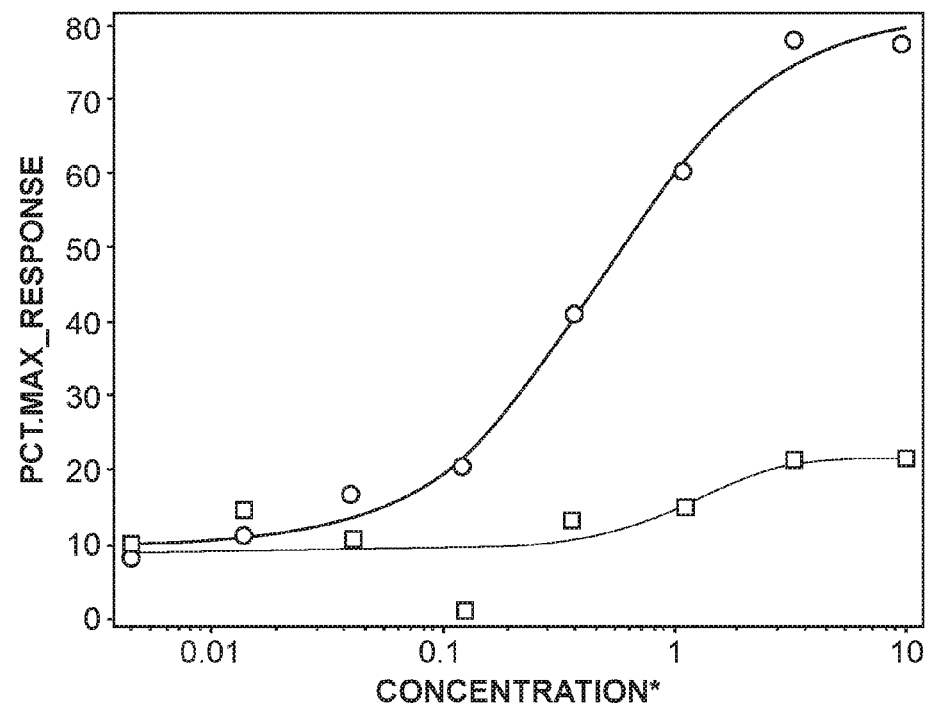
FIG. 2(B) shows that Formula I (squares) does not activate pMEK in B9 cell lines in comparison to vemurafenib (circles). Vemurafenib Mean EC$_{50}$=0.588 µM (n=26); Formula I Mean EC$_{50}$=10 µM (n=14).
Figure 2C:
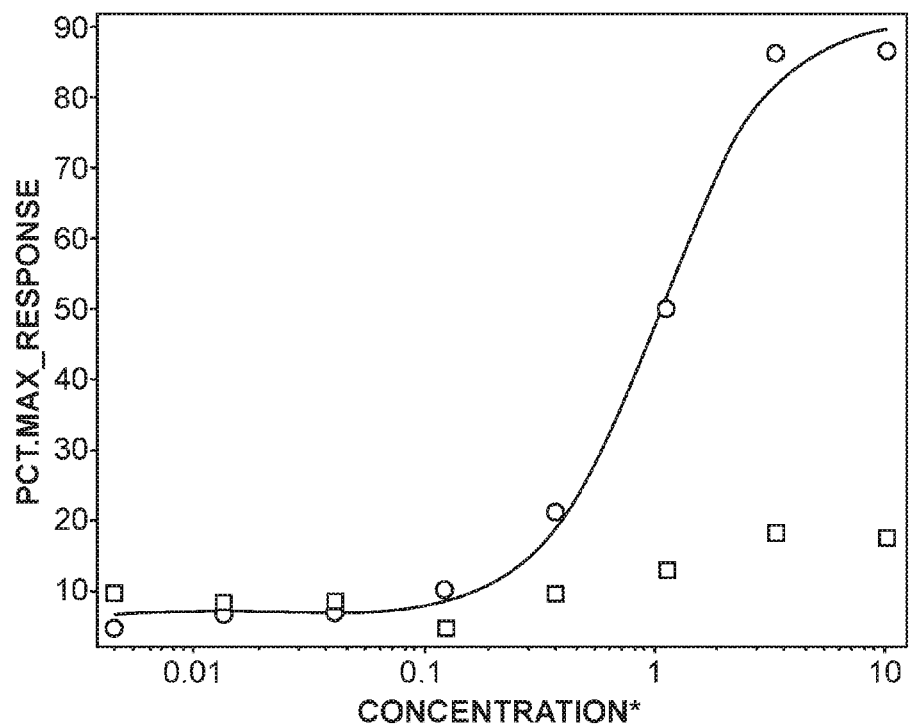
FIG. 2(C) shows that Formula I (squares) does not activate pERK in IPC-298 cell lines in comparison to vemurafenib (circles). Vemurafenib Mean EC$_{50}$=0.84 µM (n=26); Formula I Mean EC$_{50}$=10 µM (n=14).
Figure 2D:
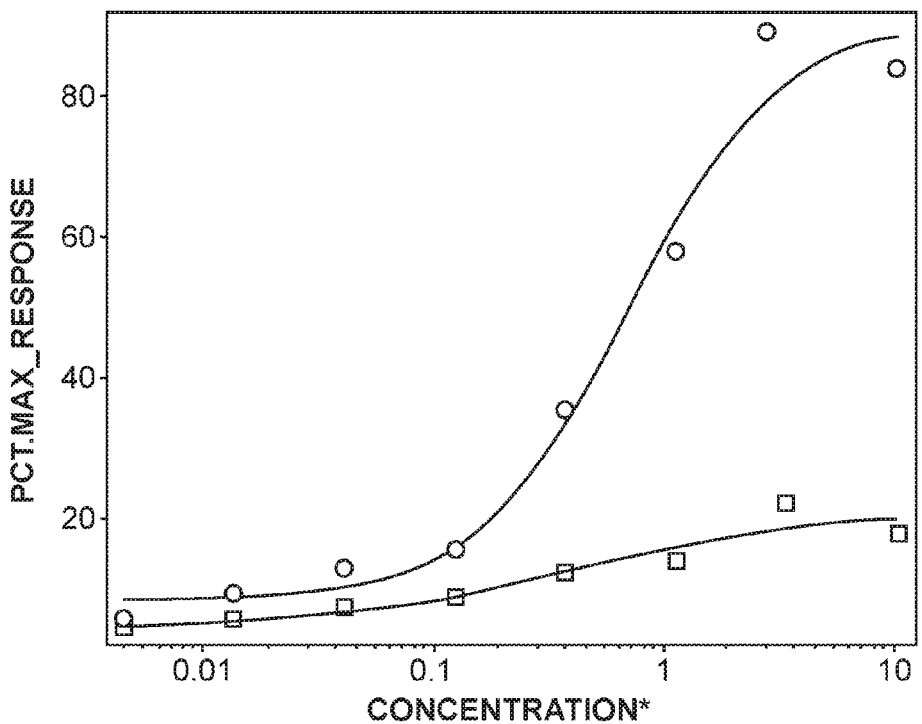
FIG. 2(D) shows that Formula I (squares) does not activate pMEK in IPC-298 cell lines in comparison to vemurafenib (circles). Vemurafenib Mean EC$_{50}$=1.011 µM (n=26); Formula I Mean EC$_{50}$=10 µM (n=14).
Figure 2E:
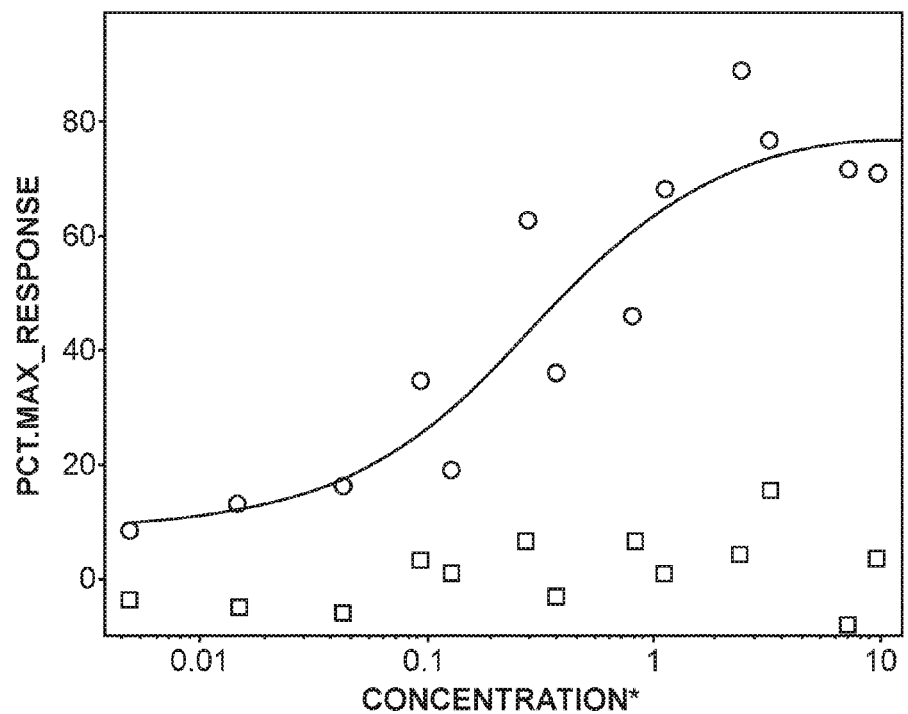
FIG. 2(E) shows that Formula I (squares) does not activate pERK in HCT116 cell lines in comparison to vemurafenib (circles). Vemurafenib Mean EC$_{50}$=0.286 µM (n=3); Formula I Mean EC$_{50}$=10 µM (n=1).
Figure 2F:
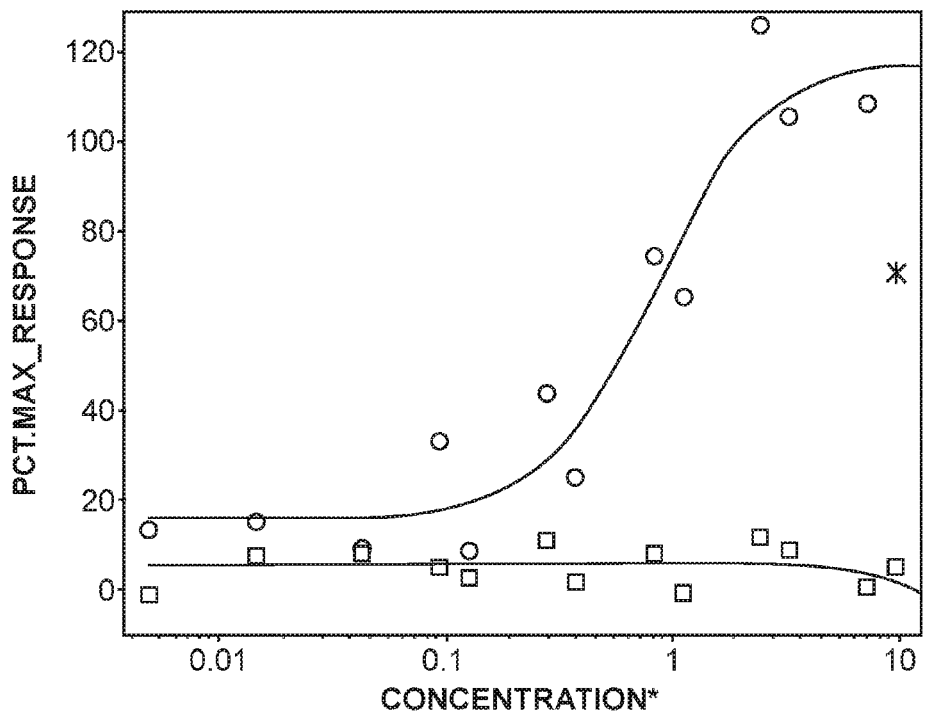
FIG. 2(F) shows that Formula I (squares) does not activate pMEK in HCT116 cell lines in comparison to vemurafenib (circles). Vemurafenib Mean EC$_{50}$=0.769 µM (n=3); Formula I Mean EC$_{50}$=10 µM (n=1).

FIG. 1(B) shows that in RAS activated human melanoma cell line IPC-298 (NRAS$^{Q61L}$), vemurafenib (open circle)

paradoxically activates MAPK signaling while Formula II (filled in circle) causes negligible pERK increase.

Based on these results, the compounds of Formula I and II are not expected to affect the MAPK pathway in normal tissues (either paradoxical activation or inhibition) at therapeutic concentrations. The pERK curves were generated using an AlphaScreen® assay. Mean±s.d., n=5 independent experiments.

Example 2: Compound of Formula I Inhibits the MEK and ERK Phosphorylation in BRAFV600 Mutant Cells and Exhibits No Paradoxical MAPK Pathway Activation in NRAS Mutant Cells MEK and ERK kinases act downstream of RAS/RAF in growing cells. Their catalytic activity is tightly associated with phosphorylation at specific residues. MEK is phosphorylated by RAF kinases at serines 217 and 221, resulting in increased MEK enzyme activity. MEK subsequently phosphorylates ERK at threonine 202 and tyrosine 204, inducing ERK catalytic activity. Cell lines that express BRAF mutated at V600 exhibit high levels of both MEK and ERK phosphorylation. First generation RAF inhibitors (e.g. dabrafenib, vemurafenib) exhibit dramatic inhibition of MEK and ERK phosphorylation and activity in BRAF-V600 mutant cells (Tsai 2008, Bollag 2010). However, these inhibitors also exhibit a paradoxical activation of MEK and ERK in cells that express mutant RAS or high levels of constitutively active growth factor receptors (Poulikakos 2010, Hatzivassiliou 2010). This is particularly concerning in light of the development of squamous cell carcinomas in patients treated with vemurafenib (Su 2012). The compound of Formula I was found to have surprising activity as a "paradox breaker" compound that retains the ability to inhibit MEK and ERK phosphorylation in BRAF-V600 mutant cells, while avoiding the paradoxical activation of the pathway in RAS mutant cells. This example demonstrates these specific characteristics of the compound of Formula I.

In order to determine the effect of the compound of Formula I on ERK and MEK phosphorylation in cells, assays using AlphaScreen® technology have been established. In cells expressing mutant BRAF-V600 (e.g. A375, COLO829, SK-MEL-3, HT-29), the constitutive catalytic activity of BRAF results in increased phosphorylation levels of the downstream effectors ERK and MEK. Inhibition of BRAF-V600 results in inhibition of ERK and MEK phosphorylation in these cells. In cells expressing mutated RAS (e.g. B9 and IPC-298), treatment with first generation RAF inhibitors (e.g. vemurafenib) results in increased phosphorylation of ERK and MEK, while Formula I did not exhibit this paradoxical activation.

Using AlphaScreen® technology, the ability of Formula I to affect the phosphorylation of ERK and MEK in the cells was measured quantitatively. Following treatment with compound, the cells were lysed, and a sample of the lysate was transferred to an assay plate. The lysate was mixed with antibodies directed against total ERK/MEK, antibodies that recognize specific phosphorylation sites on ERK/MEK, AlphaScreen® anti-mouse IgG Acceptor beads, and Streptavidin Donor beads. Upon excitation of the donor beads with laser light at 680 nm, singlet oxygen was produced. This singlet oxygen was rapidly quenched, unless the AlphaScreen® Acceptor beads were in close proximity, in which case a proximity signal can be measured at 580 nm. In the presence of phosphorylated ERK/MEK, there is a very strong proximity signal. BRAF-V600 inhibitors affect a decrease in this proximity signal in cells expressing BRAF-V600E (e.g. A375) through a decrease in phosphorylation of the BRAF effectors ERK and MEK. Additionally, Formula I did not exhibit an increase in the proximity signal in cells expressing mutant RAS (e.g. B9 and IPC-298), in contrast to vemurafenib.

1. Materials and Methods
   A. Reagents
      1. Cell Lines
   A375 Melanoma, expresses homozygous BRAF-V600E ATCC® CRL-1619™
   COLO829 Melanoma, expresses heterozygous BRAF-V600E ATCC® CRL-1974™
   HT-29 Colorectal adenocarcinoma, expresses heterozygous BRAF-V600E ATCC® HTB-38™
   SK-MEL-3 Melanoma, expresses heterozygous BRAF-V600E ATCC® HTB-69™
   B9 Squamous cell carcinoma, expresses HRAS-Q61L Received from Allan Balmain, Ph.D. (University of California, San Francisco)
   IPC-298 Melanoma, expresses NRAS-Q61L DSMZ #ACC 251
   A431 Squamous cell carcinoma, expresses high levels of EGFR, wild-type BRAF & RAS ATCC® CRL-1555™
   HCT116 Colorectal carcinoma, expresses high levels of EGFR, KRAS-G13D, wild-type BRAF ATCC® CCL-247™
      2. Cell Culture Media
   A375 & A431 Dulbecco's Modified Eagle's Medium (DMEM), ATCC #30-2002 10% Fetal Bovine Serum, Invitrogen #10438-026 1% Penicillin-Streptomycin, Invitrogen #15140-122
   B9 Dulbecco's Modified Eagle's Medium (DMEM), Invitrogen #10313-039 10% Fetal Bovine Serum, Invitrogen #10438-026 1% L-Glutamine, Invitrogen #25030-081 1% Penicillin-Streptomycin, Invitrogen #15140-122
   COLO829 & IPC-298 RPMI Medium 1640, Invitrogen #11875-119 10% Fetal Bovine Serum, Invitrogen #10438-026 1% Penicillin-Streptomycin, Invitrogen #15140-122
   SK-MEL-3 McCoy's 5A (Modified) Medium, Invitrogen #16600-108 15% Fetal Bovine Serum, Invitrogen #10438-026 1% Penicillin-Streptomycin, Invitrogen #15140-122
   HCT116 & HT-29 McCoy's 5A (Modified) Medium, Invitrogen #16600-108 10% Fetal Bovine Serum, Invitrogen #10438-026 1% Penicillin-Streptomycin, Invitrogen #15140-122
      3. Buffers
   Cell Lysis Buffer (10×) Cell Signaling Technology #9803 Diluted to 1× with $H_2O$ before use
   AlphaLISA Immunoassay buffer (10×) Perkin Elmer #AL000F Diluted to 1× with $H_2O$ before use
      4. Antibodies
   p44/42 MAPK (Erk1/2) (137F5) Rabbit (Biotinylated) donor antibody Cell Signaling Technology #5013 Final concentration=1.25 nM
   Phospho-p44/42 MAPK (Erk1/2) (Thr202/Tyr204) (E10) Mouse acceptor antibody Cell Signaling Technology #9106 Final concentration=0.17 nM
   Phospho-MEK1/2 (Ser217/221) (41G9) Rabbit (Biotinylated) donor antibody Cell Signaling Technology #3958 Final concentration=0.625 nM
   MEK1/2 (L38C12) Mouse acceptor antibody Cell Signaling Technology #4694 Final concentration=0.05 nM
      5. Detection Reagent
   AlphaScreen® Mouse IgG Detection Kit, 10,000 assay points Perkin Elmer #6760606M Final concentration=20 µg/mL B. Methods 1. One day before the assay, 50,000 cells were plated in each well of a 96-well tissue-culture-treated plate (Corning #3610) in a 50 μL volume. Cells were incubated at 37° C. overnight.
2. Compounds were diluted in DMSO to 500× final concentration. Each compound was plated as an 8-point titration, using 1:3 dilutions in DMSO. The maximum concentration was about 5 mM.
3. 1 μl of compound was added to each well of a 96-well polypropylene plate (Corning #3363). For A375, COLO829, SK-MEL-3, HCT116, and HT-29, the high control was DMSO, and the low control was 10 μM PLX4720 (CAS No. 918505-84-7). For B9 and IPC-298, the high control was 3.33 μM PLX4720, and the low control was DMSO.
4. 249 μL growth media was added to compounds, diluting them 250-fold.
5. 50 μL of the diluted compound was transferred into 50 μL cells, for a 500-fold final compound dilution (maximum concentration is typically 10 μM). The compound was incubated with the cells at 37° C. for one hour.
6. The media was aspirated, and the cells were lysed in 50 μL of ice-cold 1× Cell Lysis buffer. The plates were incubated on ice for 5 minutes to allow complete lysis of the cells.
7. A mixture of biotinylated donor antibody, acceptor antibody, and anti-mouse IgG AlphaScreen® acceptor beads in 1× AlphaLISA immunoassay buffer was prepared.
8. 5 μL of lysate was transferred to a 384-well assay plate (Perkin Elmer #6005359). 5 μL of the antibody and acceptor bead mixture was added. The plates were spinned.

The ERK/MEK phosphorylation and growth assays yield sufficient data to determine that Formula I is a potent inhibitor of BRAF-V600E in both the SK-MEL-239 parental and vemurafenib-resistant C3 cell lines. Specifically, FIGS. 2(A)-2(F) demonstrate that, in contrast to vemurafenib, Formula I does not increase pERK and pMEK levels in RAS mutant cell lines.

Example 3: Inhibition of Various BRAF V600 Mutant Proteins by Formula I

BRAF proteins were produced in insect cells at Plexxikon Inc. as N-terminally His-tagged fragments encompassing the kinase domain. Constructs encoding BRAF (S432-R726) containing the V600A, V600G, or V600M mutations and constructs BRAF(D448-K723) containing the V600E, V600K or V600R mutation were used.
BRAF
BRAF, residues L416 through H766 fused at the N-terminus with a GST tag, was produced in insect cells, and BRAF was purchased from Millipore (Catalog #14-530).
CRAF
CRAF, residues Q307 through F648 containing Y340D and Y341D activating substitutions mimicking the dual phosphorylation of Y340/341, was fused at the N-terminus with a GST tag and produced in insect cells, and CRAF was purchased from Millipore (Catalog #14-352).
Biotinylated-MEK1
MEK1, residues M1 through V393 containing kinase disabling mutation K97A, fused at the N-terminus with a GST tag and at the C-terminus with a 16 amino acid biotinylation tag was produced in *E. coli* at Plexxikon Inc.
Kinase Buffer:
50 mM HEPES, pH 7.5 50 mM NaCl 2 mM MgCl2 1 mM MnCl2 1 mM DTT 0.01% NP-40

Stop/Detection Buffer:
50 mM HEPES, pH 7.5 100 mM EDTA 0.02% BSA Anti-phospho-MEK1 (Cell Signal Technologies #9121) AlphaScreen™ donor and acceptor beads (Perkin-Elmer #6760617)

1. Methods
1) Test compounds in DMSO were serially diluted and plated into 384-well assay plates at 1 μL/well.
2) Added were 15 μL/well of RAF enzyme and biotinylated-MEK1 substrate in kinase buffer.
3) Added were 4 μL of ATP (500 μM) in kinase buffer.
4) The final DMSO was about 5%; the concentrations of RAF enzymes and MEK1 are listed in Table 2 below for each assay. Under these conditions, the enzymes were saturated with substrate; ATP was at 100 μM.

TABLE 2

| Assay | Kinase (nM) | Substrate(nM) |
| --- | --- | --- |
| BRAF_V600E | 0.015 | 15 |
| BRAF_V600A | 0.56 | 28 |
| BRAF_V600G | 0.40 | 20 |
| BRAF_V600K | 0.21 | 21 |
| BRAF_V600M | 0.56 | 28 |
| BRAF_V600R | 0.4 | 20 |
| BRAF | 0.26 | 26 |
| CRAF | 0.15 | 15 |

5) After a brief spin down, the plate was incubated at about room temperature for 40-50 minutes.
6) Added was 5 μL of Stop buffer at final EDTA 20 mM; anti-phospho-MEK1 1:2,500; donor/acceptor beads 3 μg/mL.
7) After brief spin down, the plate was incubated at room temperature for about 3 hours.
8) The plate was read on the Envision multilabel plate reader (Perkin Elmer).
$IC_{50}$ values are shown below in Table 3.

2. Results
Formula I exerts potent inhibition against V600E and all other tested non-V600E mutant BRAF proteins (Table 3). It also inhibits kinase activity of wild-type BRAF and activated CRAF (Table 3).

TABLE 3

Biochemical $IC_{50}$s against Different Forms of RAF kinases

| Kinase | Formula I $IC_{50}$ (μM) |
| --- | --- |
| BRAF | 0.0143 |
| CRAF | 0.0226 |
| BRAF_V600E | 0.0044 |
| BRAF_V600A | 0.0142 |
| BRAF_V600G | 0.0063 |
| BRAF_V600K | 0.0039 |
| BRAF_V600M | 0.0098 |
| BRAF_V600R | 0.0035 |

Example 4: Potency of the Compound of Formula I in Cell Lines Expressing Wild Type BRAF, BRAFV600E and BRAFV600K Cells ($IC_{50}$, μM) Cell Line The selective inhibition of BRAFV600E driven tumor cell proliferation by the compound of Formula I was measured in a panel of cells that harbor the mutated BRAF gene in the presence or absence of a BRAF wild type allele. BRAFV600E mutant cell lines, which were relatively resistant to vemurafenib inhibition, were also included. To demonstrate the selective mechanism of action by the compound of Formula I through inhibition of the activated BRAF protein, tumor cells that lack a mutation in BRAF and are transformed by KRAS mutation or alternate oncogenes were included. In summary, the compound of Formula I is a potent and selective inhibitor of the growth of cell lines that harbor the mutant activated BRAF protein (V600E). The compound of Formula I also inhibited cells that are resistant to vemurafenib inhibition (HT-29). Formula I's selectivity was substantiated as the proliferation of cells that harbored a mutant KRAS allele or other non-BRAF V600E mutation pathways was not affected.

In order to determine the effects of Formula I on proliferation, a growth assay was established using melanoma cells (A375 and COLO829) and colorectal carcinoma cells (COLO205, HT-29) which each express the BRAFV600E mutation. To show selectivity over wild-type BRAF, several BRAF wild-type cell lines (K562, NOMO-1, MV-4-11 and ML-2) were also examined in the growth assay. The growth assay implemented the Promega CellTiter-Glo Luminescent Cell viability assay, which gives a luminescent readout that is proportional to the amount of ATP present in a cell sample. As ATP levels directly correlate with the number of viable cells, the luminescent signal can be used to determine the potency of Formula I to block the proliferation of the cell lines of interest.

1. Materials and Methods
   A. Reagents
   1. Cell Lines
A375 Melanoma, expresses homozygous BRAFV600E; ATCC® CRL-1619™
COLO829 Melanoma, expresses heterozygous BRAFV600E; ATCC® CRL-1974™
COLO205 Colorectal adenocarcinoma, expresses heterozygous BRAFV600E; ATCC® CCL-222™
HT-29 Colorectal adenocarcinoma, expresses heterozygous BRAFV600E; ATCC® HTB-38™
K562 Chronic myelogenous leukemia (CIVIL), expresses the Philadelphia chromosome, the 9; 22 chromosomal translocation that creates BCR-ABL. It also expresses wild-type BRAF and KRAS; ATCC® CCL-243™
ML-2 Acute myelomonocytic leukemia, express activated KRAS-A146T and wild-type BRAF; DSMZ # ACC 15
MV-4-11 Biphenotypic B myelomonocytic leukemia, expresses FLT-3 ITD, wild-type BRAF and wild-type KRAS; ATCC® CRL-9591™
NOMO-1 Acute myeloid leukemia, expresses activated KRAS-G13D, and wild-type BRAF; DSMZ # ACC 542
SK-MEL-3 Melanoma, expresses heterozygous BRAF-V600E; ATCC® HTB-69™
   2. Cell Culture Media
A375 & COLO829 Dulbecco's Modified Eagle's Medium (DMEM), ATCC #30-2002 10% Fetal Bovine Serum, Invitrogen #10438-026 1% Penicillin-Streptomycin, Invitrogen #15140-122
COLO205 & NOMO-1& ML-2 RPMI Medium 1640, Invitrogen #11875-119 10% Fetal Bovine Serum, Invitrogen #10438-026 1% Penicillin-Streptomycin, Invitrogen #15140-122
HT-29 McCoy's 5A (Modified) Medium, Invitrogen #16600-108 10% Fetal Bovine Serum, Invitrogen #10438-026 1% Penicillin-Streptomycin, Invitrogen #15140-122
K562 & MV-4-11 Iscove's Modified Dulbecco's Medium (IMDM), Invitrogen#16600-108
10% Fetal Bovine Serum, Invitrogen #10438-026 1% Penicillin-Streptomycin, Invitrogen #15140-122
SK-MEL-3 McCoy's 5A (Modified) Medium, Invitrogen #16600-108 15% Fetal Bovine Serum, Invitrogen #10438-026 1% Penicillin-Streptomycin, Invitrogen #15140-122
   3. Culture Plates
Corning® 96 Well Clear V-Bottom Polypropylene Not Treated Microplate, 25 per Bag, without Lids, Nonsterile (Product #3363)
Corning® 96 Well Flat Clear Bottom White Polystyrene TC-Treated Microplates, Individually Wrapped, with Lid, Sterile (Product #3610)
   4. Detection Reagent
CellTiter-Glo® Luminescent Cell Viability Assay, Promega #G7573
   B. Methods
1. 3,000 cells were plated in each well for cell lines A375, COLO205, COLO829, HT-29, and SK-MEL-3. 25,000 cells were plated in each well for cell lines K562, ML-2, MV-4-11, and NOMO-1 of a 96-well tissue-culture-treated plate (Corning #3610) in a 50 μL volume. Cells were incubated overnight at 37° C.
2. Each test compound was plated as an 8-point titration, using 1:3 dilutions in DMSO. The maximum concentration was about 5 mM. Dilute DMSO and test compound of Formula I 1:250 in growth media.
3. 50 μL of the diluted compound was transferred into 50 μL cells, for a 500-fold final compound dilution (maximum concentration is typically 10 μM and DMSO concentration is 0.2%). The cells were incubated with DMSO/compound for 3 days at 37° C. in 5% $CO_2$.
4. Cell Titer-Glo Luminescent Assay Reagent was brought to room temperature and reconstituted as directed in the product manual. The cell cultures were also brought to room temperature for about 20-30 minutes. A 25 μL volume of reconstituted Cell Titer-Glo reagent was added to the cells, and the mixture was incubated at room temperature for about 10 minutes to ensure lysis of the cells.
5. Luminescence was measured on a Tecan Safire plate reader.

2. Results
The results are summarized in Table 4 below.

TABLE 4

| Cell Line | Tumor of Origin | BRAF (Genotype) | RAS (Genotype) | Formula I ($IC_{50}$ in μM) |
|---|---|---|---|---|
| K562 | Chronic myeloid leukemia | WT | WT | >10 |
| ML-2 | acute myelomonocytic leukemia | WT | KRAS-A146T | >10 |
| MV-4-11 | biphenotypic B myelomonocytic leukemia | WT | WT | >10 |
| NOMO-1 | acute myeloid leukemia | WT | KRAS-G13D | >10 |
| A375 | melanoma | V600E | WT | 0.05 |
| Colo205 | colorectal adenocarcinoma | V600E/WT | WT | 0.01 |
| Colo829 | melanoma | V600E/WT | WT | 0.1 |
| HT-29 | colorectal adenocarcinoma | V600E/WT | WT | 0.84 |

The compound of Formula I was a potent inhibitor in the heterozygous (COLO205, COLO829, HT-29) and homozygous BRAFV600E (A375) expressing cell lines. Specifically, the above results demonstrate that Formula I inhibited the in vitro growth of two melanoma cell lines (A375 and COLO829) and additional colorectal cancer cell lines COLO205 and HT29 that express BRAFV600E. The selectivity of Formula I is clearly demonstrated by the lack of inhibition in the BRAF wild-type cell lines K562, ML-2, NOMO-1 and MV-4-11.

Example 5: NIH/3T3 Cells Stably Expressing KIAA1549-BRAF Fusions Display Accelerated Tumor Growth in the Presence of PLX4720 Whereas Formula I Inhibits the Growth of BRAF Fusion Xenografts NIH/3T3 (ATCC® CRL-1658™) cells stably expressing KIAA1549-BRAF fusions (Fusion-1, Fusion-2, Fusion-3, and Fusion-4) were injected into the flank of balb/c nu/nu mice. Tumor growth was measured with calipers. Ellipsoid tumor volume was calculated using the following formula: volume=½·length·width$^2$.

Figure 3:
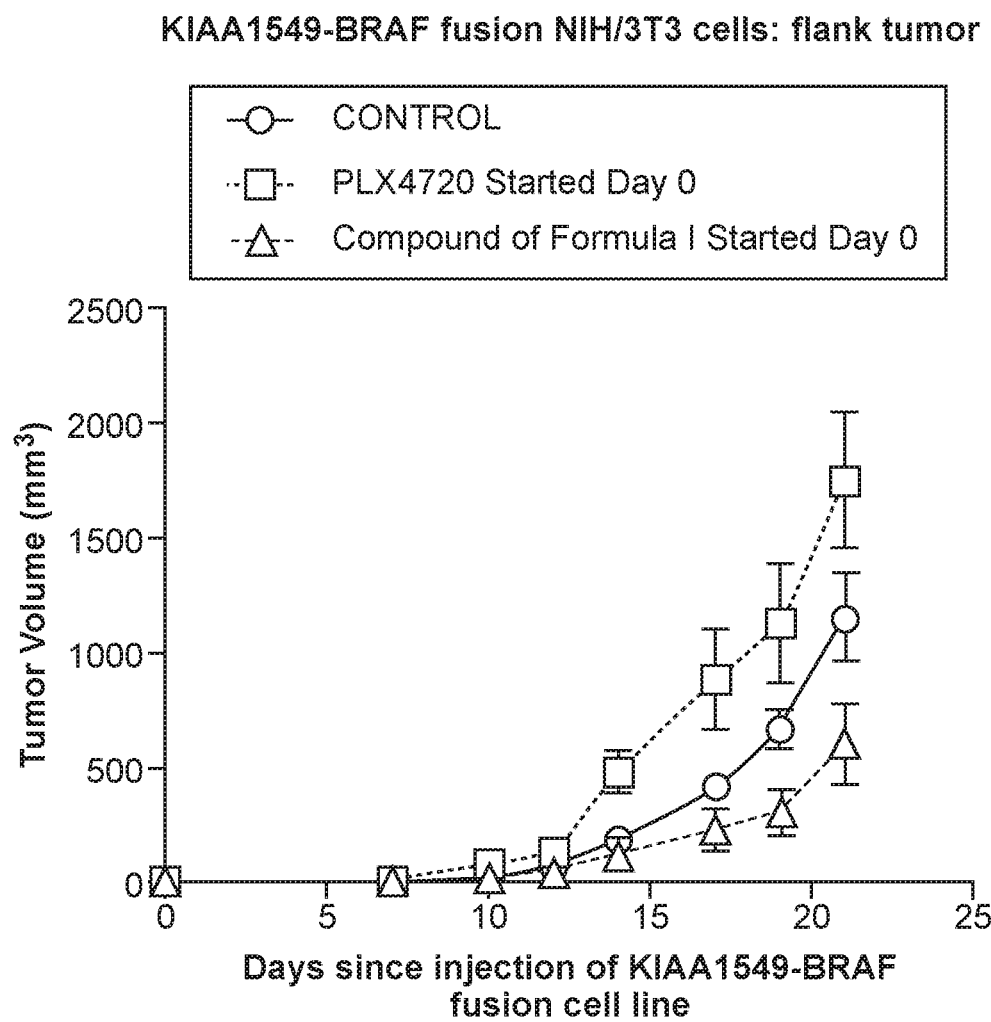
FIG. 3 shows that Formula I inhibited the growth of all three xenografts (NIH/3T3 cells expressing three of the four KIAA1549-BRAF fusions) by 50% or more. Control: circle; PLX4720: square; Formula I: triangle. They axis indicates tumor volume in cubic millimeters; the x axis indicates days since injection.

NIH/3T3 cells expressing three of the four KIAA1549-BRAF fusions demonstrated resistance and increased tumor growth in vivo when injected into the flank of immune-compromised balb/c nu/nu mice dosed with PLX4720 (CAS No. 918505-84-7; PLX4720 can be synthesized as described in Tsai et al. 2008) chow. The compound of Formula I inhibited the growth of all three xenografts (NIH/3T3 cells expressing three of the four KIAA1549-BRAF fusions) by 50% or more (FIG. 3; they axis indicates tumor volume in cubic millimeters; the x axis, days since injection). These data suggest that the compound of Formula I can successfully target KIAA1549-BRAF fusions characterizing pediatric astrocytomas and provides support for the application of this compound in BRAF-fusion-mediated cancers.

Example 6: Synthetic Examples for the Compounds of Formula I and Formula II

All solvents and reagents were used as obtained from commercial sources. Starting materials were purchased from commercial sources or prepared according to methods reported in the literature. Reactions involving air or moisture sensitive reagents were carried out under a nitrogen atmosphere. NMR spectra were recorded in deuterated solvent with an Agilent 400 MHz MR DD2 spectrometer system equipped with an Oxford AS400 magnet. Chemical shifts are expressed as ϱ units and referenced to the residual $^1$H solvent signal. All coupling constants (J) are reported in Hertz (s=singlet, d=doublet, t=triplet, q=quartet, m=multiplet, br=broad peak, dd=doublet of doublets, ddd=doublet of doublet of doublets, dm=doublet of multiplets). Mass spectra analytical purity were measured with a Shimadzu LCMS-2020 spectrometer coupled to a Shimadzu 20A HPLC system operating in reverse mode. Analytical purity was greater than 95% for final compounds and was determined using the following High Performance Liquid Chromatography ("HPLC") method: Buffer A: 5% acetonitrile, 95% water, 0.01% formic acid, buffer B: 95% acetonitrile, 5% water, 0.01% formic acid, SiliaChrom XDB C18, 5 μm, 2.1×50 mm, 5-95% B in 6 minutes, 1.0 ml/minute, 220 nm and 254 nm, ESI positive, 300-800 amu.

Synthesis of 2,6-difluoro-3-nitrobenzoyl chloride. 2,6-difluoro-3-nitrobenzoic acid (200 g, 0.985 mol) was added to thionyl chloride (737 mL, 10.2 mol) and the reaction was stirred at 80° C. for 16 hours and then allowed to cool to room temperature. The volatiles were removed under reduced pressure and the resulting oil was dissolved in toluene. The toluene was removed under reduced pressure. The addition and removal of toluene was repeated several times to provide the title compound as an oil that was used directly in the next step (218 g).

Synthesis of (2,6-difluoro-3-nitrophenyl)(5-iodo-1H-pyrrolo[2,3-b]pyridin-3-yl)methanone. 5-iodo-1H-pyrrolo[2,3-b]pyridine (160 g, 0.656 mol) and aluminum chloride (525 g, 3.94 mol) in nitromethane (1640 mL) were allowed to stir at room temperature for 1 hour. Then 2,6-difluoro-3-nitrobenzoyl chloride (218 g, 0.985 mmol) in nitromethane (1640 mL) was added and the mixture was heated at 50° C. for 4 days. After cooling to 0° C., the reaction was quenched with the dropwise addition of methanol (1.5 L) resulting in a precipitate. The mixture was diluted with water (2 L) and filtered. The crude product was triturated with methyl tert-butyl ether and filtered to give the title compound as a tan solid which was used directly in the next step (281 g).

Synthesis of (3-amino-2,6-difluorophenyl)(5-iodo-1H-pyrrolo[2,3-b]pyridin-3-yl)methanone. To (2,6-difluoro-3-nitrophenyl)(5-iodo-1H-pyrrolo[2,3-b]pyridin-3-yl)methanone (281 g, 656 mmol) in ethyl acetate (10.9 L) and tetrahydrofuran (10.9 L) was added tin(II) chloride dihydrate (517 g, 2.72 mol) portion wise while heating at 60° C. The reaction mixture was held at this temperature overnight. After cooling to room temperature, the reaction mixture was quenched with 50% saturated aqueous sodium bicarbonate (1:1 water and saturated aqueous sodium bicarbonate) and filtered through Celite washing the cake with ethyl acetate. The layers were separated and the organic layer was washed with brine and then concentrated under reduced pressure to give the crude product which was triturated with methyl tert-butyl ether and filtered to give the title compound as a tan solid (216 g, 541 mmol, 83% yield, ~85% purity).

Synthesis of (3-amino-2,6-difluorophenyl)(5-(2-cyclopropylpyrimidin-5-yl)-1H-pyrrolo[2,3-b]pyridin-3-yl)methanone. A mixture of (3-amino-2,6-difluorophenyl)(5-iodo-1H-pyrrolo[2,3-b]pyridin-3-yl)methanone (93 g, 233 mmol), 2-cyclopropyl-5-(4,4,5,5-tetramethyl-1,3,2-dioxaborolan-2-yl)pyrimidine (229 g, 466 mmol, ~50% purity), potassium carbonate (97 g, 700 mmol) and [1,1'-bis(diphenylphosphino)ferrocene]dichloropalladium(II) (19.0 g, 23.3 mmol) in dioxane (930 mL) and water (465 mL) was heated at 100° C. for several hours. Upon cooling, the reaction mixture was diluted with water and extracted with a mixture of tetrahydrofuran and ethyl acetate. The organic layer was separated and concentrated under reduced pressure to give the crude product which was triturated with dichloromethane/methyl tert-butyl ether and filtered, washing with methyl tert-butyl ether to give the title compound as a tan solid (71 g, 78% yield).

Synthesis of 5-(2-cyclopropylpyrimidin-5-yl)-3-[3-[[ethyl(methyl)sulfamoyl]amino]-2,6-difluoro-benzoyl]-1H-pyrrolo[2,3-b]pyridine (Formula II). To (3-amino-2,6-difluorophenyl)(5-(2-cyclopropylpyrimidin-5-yl)-1H-pyrrolo[2,3-b]pyridin-3-yl)methanone (53.8 g, 138 mmol) in pyridine (1375 mL) was added ethyl(methyl)sulfamoyl chloride (65.0 g, 412 mmol) and the reaction was heated at 65° C. overnight. The volatiles were removed under reduced pressure and the residue was partitioned between water and ethyl acetate/tetrahydrofuran. The organic layer was concentrated under reduced pressure to give the crude product which was dry loaded onto silica gel and purified by silica gel column chromatography (2×) eluting with 0-10% methanol/dichloromethane then (1×) eluting ethyl acetate. The fractions containing the desired product were pooled and concentrated under reduced pressure. The resulting solid was triturated with methyl tert-butyl ether and filtered to give the title compound as a white solid (21 g). $^1$H NMR (400 MHz, DMSO-d$_6$) 13.07 (br s, 1H), 9.71 (br s, 1H), 9.03

(s, 2H), 8.76 (s, 1H), 8.68 (s, 1H), 8.19 (s, 1H), 7.59 (ddd, J=5.9 Hz, 9.0 Hz, 9.0 Hz, 1H), 7.27 (dd, J=9.0 Hz, 9.0 Hz, 1H), 3.12 (q, J=7.0 Hz, 2H), 2.74 (s, 3H), 2.29 (m, 1H), 1.09 (m, 4H), 0.95 (t, J=7.0 Hz, 3H). LC/MS (ESI+) m/z: 513.3 (M+H$^+$).

Synthesis of (3R)—N-[3-[5-(2-cyclopropylpyrimidin-5-yl)-1H-pyrrolo[2,3-b]pyridine-3-carbonyl]-2,4-difluoro-phenyl]-3-fluoro-pyrrolidine-1-sulfonamide (Formula I). This material was prepared in a manner analogous to Formula II using (3R)-3-fluoropyrrolidine-1-sulfonyl chloride in place of ethyl(methyl)sulfamoyl chloride. The product was purified by reverse phase HPLC to provide, after lyophilization, the title compound as a white solid. $^1$H NMR (400 MHz, DMSO-d6) 13.05 (br s, 1H), 9.84 (br s, 1H), 9.01 (s, 2H), 8.73 (s, 1H), 8.67 (s, 1H), 8.15 (s, 1H), 7.62 (ddd, J=5.9 Hz, 9.0 Hz, 9.0 Hz, 1H), 7.26 (dd, J=9.0 Hz, 9.0 Hz, 1H), 5.29 (dm, J=51.6 Hz (H—F), 1H), 3.43 (dm, 2H), 3.33 (m, 2H), 2.27 (m, 1H), 2.04 (m, 2H), 1.06 (m, 4H). LC/MS (ESI+) m/z: 542.9 (M+H$^+$).

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

The disclosure illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the disclosure using one of the terms, the disclosure also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described disclosure.

Thus, additional embodiments are within the scope of the disclosure and within the is following claims.

What is claimed is:

1. A method of treating or inhibiting a BRAF V600 mutation or BRAF fusion mutation related disease or condition, without activating the MAPK pathway or inducing expression of MAPK pathway genes in cells harboring wild-type BRAF, in a subject suffering from or at risk for a said disease or condition, comprising administering to the subject in need thereof a therapeutically effective amount of a compound of Formula I:

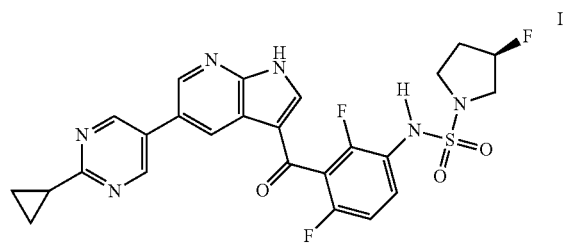 [SMILES: O=C(c1c(F)ccc(NS(=O)(=O)N2CC[C@@H](F)C2)c1F)c1c[nH]c2ncc(-c3cnc(C4CC4)nc3)cc12]

or a pharmaceutically acceptable salt, isomer, tautomer or deuterated form thereof.

2. The method according to claim 1, wherein the non-activation of the MAPK pathway or non-inducement of expression of MAPK pathway genes in cells harboring wild-type BRAF comprises inhibition of phosphor-ERK (pERK) in BRAF wild-type cells.

3. The method according to claim 1, wherein the non-activation of the MAPK pathway or non-inducement of expression of the MAPK pathway comprises inhibition of pERK and pMEK in BRAF wild-type cells.

4. The method according to claim 1, wherein the non-activation of the MAPK pathway or non-inducement of expression of MAPK pathway genes in cells harboring wild-type BRAF inhibits stimulation of cell growth.

5. The method according to claim 1, wherein the non-activation of the MAPK pathway or non-inducement of expression of MAPK pathway genes in cells harboring wild-type BRAF inhibits stimulation of skin neoplasms.

6. The method according to claim 1, wherein the therapeutically effective amount of Formula I is administered in a pharmaceutical composition further comprising a pharmaceutically acceptable excipient or carrier.

7. The method according to claim 1, wherein the therapeutically effective amount of Formula I is administered in a pharmaceutical composition further comprising another therapeutic agent.

8. The method according to claim 1, wherein the BRAF V600 mutation or BRAF fusion mutation related disease or condition is melanoma, colorectal cancer, papillary thyroid cancer, anaplastic thyroid cancer, ovarian cancer, non-small-cell lung cancer, gastric cancer, cholangiocarcinoma, Barrett's esophageal cancer, head and neck cancer, hepatocellular carcinoma, Langerhan's cell histiocytosis, gastrointestinal stromal cell tumours, multiple myeloma, pediatric astrocytomas, pleomorphic xanthoastrocytomas, chronic myeloid leukemia, acute myelomonocytic leukemia, biphenotypic B myelomonocytic leukemia, acute myeloid leukemia, hairy cell leukemia, nevi, Erdheim-Chester disease, malignant peripheral nerve sheath tumor, inflammatory and autoimmune disease, tenosynovial giant cell tumor, pigmented villonodular synovitis, giant cell tumor of tendon sheath, giant cell tumor of bone, cervical cancer, endometrial cancer, germ cell tumors, prostate cancer, bladder cancer, myopericytoma, metanephric adenoma, pancreatic neoplasms, neuroendocrine tumors, endocrine tumors, adrenal tumors, adrenal medullary tumors, cystadenocarcinoma of the parotid, glioblastoma multiforme, bile duct cancer including bile duct adenoma, B-cell chronic lymphoproliferative disorder, dendritic cell sarcomas, histiocytic sarcomas, or lymphoma.

9. The method according to claim 1, wherein the BRAF V600 mutation or BRAF fusion mutation related disease or condition is hepatocellular carcinoma, Langerhan's cell histiocytosis, gastrointestinal stromal cell tumours, multiple myeloma, pediatric astrocytomas, pleomorphic xanthoastrocytomas, chronic myeloid leukemia, acute myelomonocytic leukemia, biphenotypic B myelomonocytic leukemia, acute myeloid leukemia, hairy cell leukemia, or nevi.

10. The method according to claim 1, wherein the BRAF V600 mutation or BRAF fusion mutation related disease or condition is melanoma, colorectal cancer, papillary thyroid cancer, anaplastic thyroid cancer, ovarian cancer, non-small-cell lung cancer, gastric cancer, cholangiocarcinoma, Barrett's esophageal cancer, or head and neck cancer.

11. The method according to claim 1, wherein the BRAF V600 mutation related disease or condition is Erdheim-Chester disease.

12. The method according to claim 1, wherein the BRAF V600 mutation related disease or condition is melanoma.

13. The method according to claim 1, wherein the BRAF V600 mutation related disease or condition is metastatic melanoma.

14. The method according to claim 1, wherein the BRAF V600 mutation related disease or condition is colorectal cancer.

15. The method according to claim 1, wherein the BRAF V600 mutation related disease or condition is papillary thyroid cancer.

16. The method according to claim 1, wherein the BRAF V600 mutation related disease or condition is anaplastic thyroid cancer.

17. The method according to claim 1, wherein the BRAF V600 mutation related disease or condition is ovarian cancer.

18. The method according to claim 1, wherein the BRAF V600 mutation related disease or condition is non-small-cell lung cancer.

19. The method according to claim 1, wherein the BRAF V600 mutation related disease or condition is gastric cancer.

20. The method according to claim 1, wherein the BRAF V600 mutation related disease or condition is Langerhan's cell histiocytosis.

21. The method according to claim 1, wherein the BRAF V600 mutation related disease or condition is acute myeloid leukemia.

22. The method according to claim 1, wherein the BRAF V600 mutation related disease or condition is multiple myeloma.

23. The method according to claim 1, wherein the BRAF V600 mutation related disease or condition is malignant peripheral nerve sheath tumor.

24. The method according to claim 1, wherein the BRAF fusion mutation related disease or condition is pediatric astrocytomas.

25. The method according to claim 1, wherein the BRAF V600 mutation is one or more mutations selected from the group consisting of V600E, V600K, V600D, V600A, V600G, V600M, and V600R.

26. The method according to claim 1, wherein the BRAF V600 mutation comprises a V600E mutation and a V600K mutation.

27. The method according to claim 1, wherein the BRAF V600 mutation comprises a V600E mutation.

28. The method according to claim 1, further comprising administering to said subject one or more of the following agents: adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, uramustine, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, zorubicin, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, vidarabine, alemtuzumab, pembrolizumab, nivolumab, bevacizumab, cetuximab, galiximab, gemtuzumab, panitumumab, pertuzumab, rituximab, tositumomab, trastuzumab, 90Y-ibritumomab tiuxetan, ipilimumab, tremelinuimab, anastrozole, androgens, buserelin, diethylstilbestrol, exemestane, flutamide, fulvestrant, goserelin, idoxifene, letrozole, leuprolide, magestrol, raloxifene, tamoxifen, toremifene, DJ-927, docetaxel, TPI 287, larotaxel, ortataxel, paclitaxel, DHA-paclitaxel, tesetaxel, alitretinoin, bexarotene, fenretinide, isotretinoin, tretinoin, demecolcine, homoharringtonine, vinblastine, vincristine, vindesine, vinflunine, vinorelbine, an antiangiogenic agent, including, but not limited to, Neovastat, ABT-510, 2-methoxyestradiol, lenalidomide, thalidomide, amsacrine, edotecarin, etoposide, etoposide phosphate, exatecan, irinotecan, lucanthone, mitoxantrone, pixantrone, rubitecan, teniposide, topotecan, 9-aminocamptothecin, axitinib, erlotinib, gefitinib, flavopiridol, imatinib mesylate, cabozantinib, lapalinib, motesanib diphosphate, nilotinib, seliciclib, sorafenib, sunitinib malate, AEE-788, BMS-599626, 7-hydroxystaurosporine, vatalanib, bortezomib, geldanamycin, rapamycin, imiquimod, interferon-a, interleukin-2, 3-amino-2-carboxyaldehyde thiosemicarbazone, altrasentan, aminoglutethimide, anagrelide, asparaginase, bryostatin-1, cilengitide, elescloniol, eribulin mesylate, ixabepilone, lonidamine, masoprocol, mitoguanazone, oblimersen, sulindac, testolactone, tiazofurin, temsirolimus, everolimus, deforolimus, a PI3K inhibitor, a Cdk4 inhibitor, a Akt inhibitor, a Hsp90 inhibitor, an EGFR inhibitor, an IDO inhibitor, a farnesyltransferase inhibitor, a MEK inhibitor, a BET inhibitor, AS703026, selumetinib, AZD8330, BIX02188, PD184352, D-87503, GS 1 120212, PD0325901, PD3 18088, PD98059, PDEA1 19, or TAK-733.

29. The method according to claim 7, wherein the another therapeutic agent is adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosfamide, uramustine, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, zorubicin, aminopterin, azacitidine, azathioprine, capecitabine, cladribine, clofarabine, cytarabine, decitabine, floxuridine, fludarabinc, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, vidarabine, alemtuzumab, pembrolizumab, nivolumab, bevacizumab, cetuximab, galiximab, gemtuzumab, panitumumab, pertuzumab, rituximab, tositumomab, trastuzumab, 90Y-ibritumomab tiuxetan, ipilimumab, tremelinuimab, anastrozole, androgens, buserelin, diethylstilbestrol, exemestane, flutamide, fulvestrant, goserelin, idoxifene, letrozole, leuprolide, magestrol, raloxifene, tamoxifen, toremifene, DJ-927, docetaxel, TPI 287, larotaxel, ortataxel, paclitaxel, DHA-paclitaxel, tesetaxel, alitretinoin, bexarotene, fenretinide, isotretinoin, tretinoin, demecolcine, homoharringtonine, vinblastine, vincristine, vindesine, vinflunine, vinorelbine, an antiangiogenic agent, including, but not limited to, Neovastat, ABT-510, 2-methoxyestradiol, lenalidomide, thalidomide, amsacrine, edotecarin, etoposide, etoposide phosphate, exatecan, irinotecan, lucanthone, mitoxantrone, pixantrone, rubitecan, teniposide, topotecan, 9-aminocamptothecin, axitinib, erlotinib, gefitinib, flavopiridol, imatinib mesylate, cabozantinib, lapalinib, motesanib diphosphate, nilotinib, seliciclib, sorafenib, sunitinib malate, AEE-788, BMS-599626, 7-hydroxystaurosporine, vatalanib, bortezomib, geldanamycin, rapamycin, imiquimod, interferon-a, interleukin-2, 3-amino-2-carboxyaldehyde thiosemicarbazone, altrasentan, aminoglutethimide, anagrelide, asparaginase, bryostatin-1, cilengitide, elescloniol, eribulin mesylate, ixabepilone, lonidamine, masoprocol, mitoguanazone, oblimersen, sulindac, testolactonc, tiazofurin, temsirolimus, everolimus, deforolimus, a PI3K inhibitor, a Cdk4 inhibitor, a Akt inhibitor, a Hsp90 inhibitor, an EGFR inhibitor, an IDO inhibitor, a farnesyltransferase inhibitor, a MEK inhibitor, a BET inhibitor, AS703026, selumetinib, AZD8330, BIX02188, PD184352, D-87503, GS 1 120212, PD0325901, PD3 18088, PD98059, PDEAl 19, or TAK-733.

30. The method according to claim 1, wherein the BRAF V600 mutation related disease or condition is cholangiocarcinoma.

31. method according to claim 1, wherein the BRAF V600 mutation related disease or condition is glioblastoma multiforme.

* * * * *